(12) United States Patent
Bratbak et al.

(10) Patent No.: US 10,716,834 B2
(45) Date of Patent: Jul. 21, 2020

(54) INTERVENTION DEVICE

(71) Applicant: NORWEGIAN UNIVERSITY OF SCIENCE AND TECHNOLOGY (NTNU), Trondheim (NO)

(72) Inventors: Daniel Fossum Bratbak, Trondheim (NO); Ståle Nordgård, Heimdal (NO)

(73) Assignee: Norwegian University of Science and Technology (NTNU), Trondheim (NO)

( * ) Notice: Subject to any disclaimer, the term of this patent is extended or adjusted under 35 U.S.C. 154(b) by 268 days.

(21) Appl. No.: 14/426,283

(22) PCT Filed: Sep. 6, 2013

(86) PCT No.: PCT/EP2013/068508
§ 371 (c)(1),
(2) Date: Mar. 5, 2015

(87) PCT Pub. No.: WO2014/037524
PCT Pub. Date: Mar. 13, 2014

(65) Prior Publication Data
US 2015/0265769 A1 Sep. 24, 2015

(30) Foreign Application Priority Data

Sep. 6, 2012 (GB) .................................. 1215949.7
Sep. 6, 2012 (GB) .................................. 1215950.5

(51) Int. Cl.
*A61B 5/00* (2006.01)
*A61K 38/48* (2006.01)
(Continued)

(52) U.S. Cl.
CPC ...... *A61K 38/4893* (2013.01); *A61B 10/0233* (2013.01); *A61B 17/3403* (2013.01);
(Continued)

(58) Field of Classification Search
CPC .......... A61K 9/0019; A61B 2090/3941; A61B 2090/3966
(Continued)

(56) References Cited

U.S. PATENT DOCUMENTS 4,886,493 A * 12/1989 Yee .......................... A61M 11/00
604/516
5,766,605 A 6/1998 Sanders et al.
(Continued)

FOREIGN PATENT DOCUMENTS

DE 202007004191 U1 6/2007
EP 1444962 A2 8/2004
(Continued)

OTHER PUBLICATIONS

Felisati G. et al., Sphenopalatine Endoscopic Ganglion Block, The Larygoscope 116(8)1447-50, Aug. 2006.
(Continued)

*Primary Examiner* — May A Abouelela
(74) *Attorney, Agent, or Firm* — Banner & Witcoff, Ltd.

(57) ABSTRACT

A device for interventions within the body, the device comprising: an end piece 6 for insertion into the body at a distal end thereof, the end piece 6 including a rigid lumen for holding an instrument 10 and guiding the instrument 10 to the distal end of the end piece; and a body section 4 supporting the lumen and being rigidly connected thereto, the body section including a navigation array 14 for guidance of the device using a surgical navigation system and/or including an anchor point 20 for a standard navigation array.

18 Claims, 11 Drawing Sheets

(51) Int. Cl.

| | | |
|---|---|---|
| *A61B 10/02* | (2006.01) | |
| *A61B 17/34* | (2006.01) | |
| *A61P 27/02* | (2006.01) | |
| *A61N 1/372* | (2006.01) | |
| *A61P 25/06* | (2006.01) | |
| *A61M 5/20* | (2006.01) | |
| *A61M 5/24* | (2006.01) | |
| *A61K 9/00* | (2006.01) | |
| *A61M 5/28* | (2006.01) | |
| *A61M 5/32* | (2006.01) | |
| *A61B 17/00* | (2006.01) | |
| *A61B 90/00* | (2016.01) | |
| *A61B 34/20* | (2016.01) | |

(52) U.S. Cl.
CPC ............ *A61K 9/0019* (2013.01); *A61M 5/20* (2013.01); *A61M 5/24* (2013.01); *A61M 5/28* (2013.01); *A61M 5/3286* (2013.01); *A61N 1/372* (2013.01); *A61P 25/06* (2018.01); *A61P 27/02* (2018.01); *A61B 2010/0208* (2013.01); *A61B 2017/00199* (2013.01); *A61B 2034/2051* (2016.02); *A61B 2034/2055* (2016.02); *A61B 2034/2068* (2016.02); *A61B 2090/372* (2016.02); *A61B 2090/397* (2016.02); *A61B 2090/3937* (2016.02); *A61B 2090/3983* (2016.02); *A61M 2005/206* (2013.01); *A61M 2209/01* (2013.01); *A61M 2210/0687* (2013.01)

(58) Field of Classification Search
USPC ........ 600/562, 564, 566, 567, 429; 606/205; 604/509, 95.01
See application file for complete search history.

(56) References Cited

U.S. PATENT DOCUMENTS

| | | | | |
|---|---|---|---|---|
| 6,021,343 | A * | 2/2000 | Foley | A61B 17/16 600/417 |
| 6,322,542 | B1 * | 11/2001 | Nilson | A61M 31/00 604/257 |
| 6,351,659 | B1 | 2/2002 | Vilsmeier | |
| 6,491,940 | B1 * | 12/2002 | Levin | A61K 31/445 424/434 |
| 7,155,316 | B2 * | 12/2006 | Sutherland | A61B 34/70 318/568.11 |
| 7,419,497 | B2 * | 9/2008 | Muni | A61B 17/24 424/434 |
| 7,725,162 | B2 * | 5/2010 | Malackowski | A61B 90/36 600/424 |
| 7,799,337 | B2 * | 9/2010 | Levin | A61K 9/0043 424/434 |
| 7,981,433 | B2 | 7/2011 | Blumenfeld | |
| 8,123,697 | B2 * | 2/2012 | Daum | A61B 90/10 600/562 |
| 8,231,588 | B2 | 7/2012 | Xia | |
| 8,388,600 | B1 * | 3/2013 | Eldredge | A61M 31/00 604/514 |
| 8,795,188 | B2 * | 8/2014 | Maschke | A61B 5/1135 600/534 |
| 8,846,622 | B2 | 9/2014 | Blumenfeld | |
| 9,060,794 | B2 * | 6/2015 | Kang | A61B 17/1622 |
| 9,364,230 | B2 * | 6/2016 | Shelton, IV | A61B 17/07207 |
| 9,622,832 | B2 * | 4/2017 | Birkenbach | A61B 90/96 |
| 2003/0208122 | A1 | 11/2003 | Melkent et al. | |
| 2005/0020909 | A1 | 1/2005 | Moctezuma De La Barrera et al. | |
| 2005/0154296 | A1 | 7/2005 | Lechner et al. | |
| 2005/0267009 | A1 | 12/2005 | Deagle | |
| 2006/0063973 | A1 | 3/2006 | Makower et al. | |
| 2006/0171963 | A1 | 8/2006 | Blumenfeld | |
| 2007/0167868 | A1 * | 7/2007 | Sauer | A61B 10/0233 600/564 |
| 2007/0208252 | A1 | 9/2007 | Makower | |
| 2008/0103509 | A1 | 5/2008 | Goldbach | |
| 2008/0185430 | A1 | 8/2008 | Goldbach | |
| 2008/0279895 | A1 | 11/2008 | Blumenfeld | |
| 2009/0012532 | A1 * | 1/2009 | Quaid | A61B 17/1764 606/130 |
| 2009/0192408 | A1 * | 7/2009 | Mark | A61B 90/39 600/562 |
| 2009/0318875 | A1 * | 12/2009 | Friedman | A61B 17/3468 604/187 |
| 2010/0030187 | A1 | 2/2010 | Xia | |
| 2010/0030188 | A1 * | 2/2010 | Xia | A61M 11/06 604/514 |
| 2010/0100081 | A1 | 4/2010 | Tuma et al. | |
| 2010/0227822 | A1 | 9/2010 | Blumenfeld | |
| 2013/0060278 | A1 * | 3/2013 | Bozung | A61B 34/20 606/205 |
| 2013/0218142 | A1 | 8/2013 | Tuma et al. | |
| 2015/0182293 | A1 * | 7/2015 | Yang | A61B 5/064 600/424 |
| 2015/0265769 | A1 | 9/2015 | Bratbak et al. | |

FOREIGN PATENT DOCUMENTS

| | | |
|---|---|---|
| EP | 1915962 A1 | 4/2008 |
| EP | 2179703 A1 | 4/2010 |
| WO | 2005000139 A1 | 1/2005 |
| WO | 2008091917 A2 | 7/2008 |
| WO | 2009107703 A1 | 9/2009 |
| WO | 2011084507 A1 | 7/2011 |

OTHER PUBLICATIONS

Miles Day, Sphenopalatine ganglion analgesia, Current Review of Pain, vol. 3, No. 5, Oct. 1, 1999 (Oct. 1, 1999), pp. 342-347, XP055287005, US, ISSN: 1069-5850, DOI: 10.1007/s11916-999-0029-6.
Dec. 18, 2012 (GB) Search Report—App 1215949.7.
Dec. 18, 2012 (GB) Search Report—App 1215950.5.
Varghese et al., Endoscopic transnasal neurolytic sphenopalatine ganglion block for head and neck cancer pain, The Journal of Larygology & Otology, May 2001, vol. 115, pp. 385-387.
Olesen, the role of nitric oxide (NO) in migraine, tension-type headache and cluster headache, Pharmacology & Therapeutics, 120 (2008) 157-171.
Cohen et al., Functional neuroimaging of primary headache disorders, Expert Rev. Neurotherapeutics, 6(8), (2006), 1159-1171.
Maizels et al., Intranasal Lidocaine for Migraine: A Randomized Trial and Open-Label Follow-up, Headache, 1999; 39(8):543-51.
Cassano et al., Sphenopalatine artery ligation with nerve resection in patients with vasomotor rhinitis and polyposis: a prospective, randomized, double-blind investigation, Acta Oto-Laryngologica, 2012;132(5):525-32.
Goadsby, Pathophysiology of cluster headache: a trigeminal autonomic cephalgia, Lancet Neurology, 2002;1:251-57.
Goadsby et al., Trigeminal automomic cephalagias: diagnostic and therapeutic developments, Current Opinion in Neurology, 2008;21:323-330.
Maizels et al., Intranasal lidocaine for treatment of migraine: a randomized, double-blind, controlled trial, JAMA, 1996;276(4):319-21.
Su et al., Antegrade transsphenoidal vidian neurectomy: Short-term surgical outcome analysis, American Journal of Rhinology & Allergy, 2011;25:e217-e220.
Yang et al., A novel approach to transnasal sphenopalatine ganglion injection, MEDLINE abstract Accession No. NLM16703973, Pain Physician, vol. 9, No. 2, 2006, pp. 131-134.
Turk et al., Botulinum toxin and intractable trigeminal neuralgia, Clinical Neuropharmacology, vol. 28, No. 4, 2005, pp. 161-162.
International Search Report and Written Opinion dated Dec. 12, 2013(PCT/EP2013/068508); ISA/EP.

(56) References Cited

OTHER PUBLICATIONS

International Search Report and Written Opinion dated Jan. 2, 2014 (PCT/EP2013/068515); ISA/EP.
Piagkou M N et al: "The Pterygopalatine Ganglion and its Role in Various Pain Syndromes: From Anatomy to Clinical Practice", EMBASE, Jun. 1, 2012 (Jun. 1, 2012), XP002717711, the whole article.
Slades G et al: "Control of lacrimal secretion after sphenopalatine ganglion block" Ophthalmic Plastic and Reconstructive Surgery, Masson, New York, NY, US, vol. 2, No. 2, Jan. 1, 1986 (Jan. 1, 1986), pp. 65-70, XP009174933, ISSN: 0740-9303, figure 2, abstract, rest of article.

\* cited by examiner

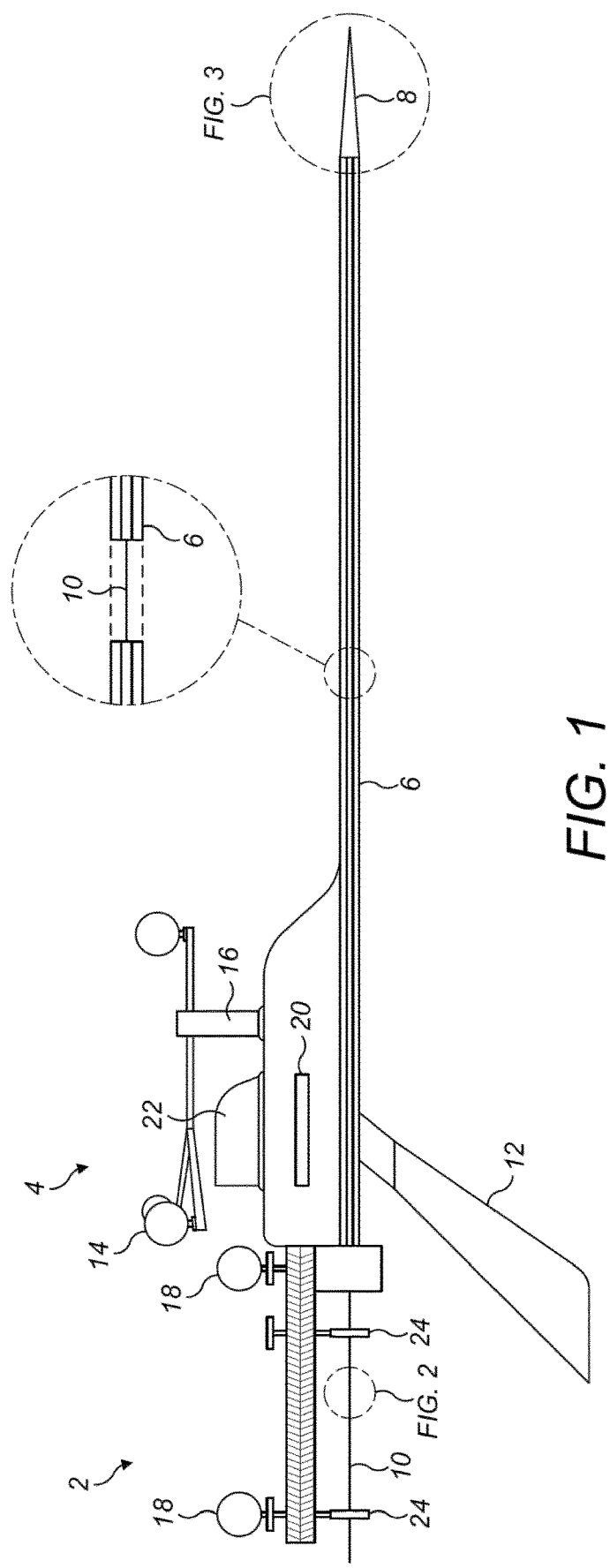
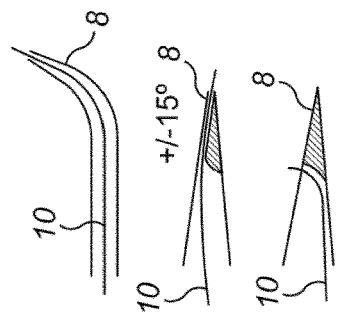
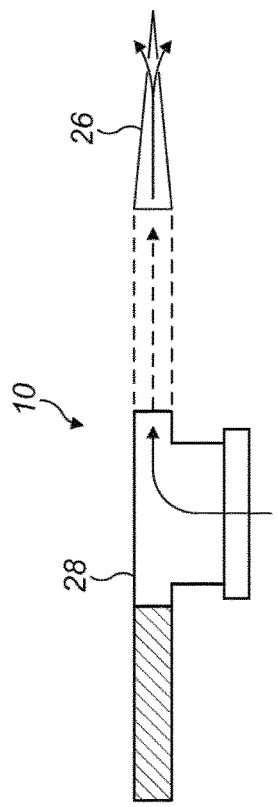
FIG. 1
FIG. 2
FIG. 3

INTERVENTION DEVICE

The present application is a U.S. National Phase filing of International Application No. PCT/EP2013/068508, filed on Sep. 6, 2013, designating the United States of America and claiming priority to British Patent Application No. 1215950.5 filed Sep. 6, 2012 and British Patent Application No. 1215949.7 filed Sep. 6, 2012. The present application claims priority to and the benefit of all the above-identified applications, which are all incorporated by reference herein in their entireties.

This disclosure relates to a device for interventions within the body, for example for injection of a substance into the body or for use as a pointer. In one example the device is used for injections towards cranial parasympathetic ganglia. The disclosure also relates to the use of such a device in the treatment of medical conditions, for example in the treatment of primary headaches.

Migraine is a primary headache that may be characterized as a unilateral headache associated with symptoms like nausea, photophobia and phonophobia. More than 50% have as well cranial autonomic symptoms such as lacrimation, conjunctival injection, nasal congestion and rhinorrhoea.

A possible mechanism for a migraine attack is parasympathetic activation with nitrogen oxide (NO) as transmitter inducing dilatation of cranial blood vessels, plasma protein extravasation and release of inflammatory substances. The catalysing enzyme for NO, NOS (NO synthases), has been located in perivascular nerve fibres on cerebral arteries and traced back to the sphenopalatine ganglion (SPG) and otic ganglion (OG), as described by Olesen J. in "The role of nitric oxide (NO) in migraine, tension-type headache and cluster headache", Pharmacology and Therapeutics, 2008; 120; 157-171.

Blocking of the SPG by application of lidocaine has shown to be effective in randomised, controlled studies of acute treatment of migraine (see Maizels M, Scott B, Cohen W and Chen W, "Intranasal lidocaine for treatment of migraine: a randomized, double-blind, controlled trial" JAMA, 1996; 276(4):319-21 and Maizels M and Geiger A M, "Intranasal lidocaine for migraine: a randomized trial and open-label follow-up", Headache, 1999; 39(8):543-51). Blocking via botulinum toxin is also described in the prior art, for example in U.S. Pat. No. 7,981,433.

The trigeminal autonomic cephalalgias (TACs) are a group of primary headache disorders characterized by unilateral head pain that occurs in association with ipsilateral cranial autonomic features such as lacrimation, conjuctival injection and nasal symptoms. The TACs include hemicrania continua, paroxysmal hemicrania, short lasting unilateral neuralgiform headache with conjunctival injection and tearing/cranial autonomic features (SUNCT/SUNA) and cluster headache.

Cluster headache is a severe unilateral headache associated with ipsilateral autonomic symptoms and characterised by a circannual and circadian periodicity (see Goadsby P J, Cittadini E, Burns B and Cohen A, "Trigeminal autonomic cephalalgias: diagnostic and therapeutic developments" Curr Opin Neurol, 2008; 21:323-330). Approximately 90% suffer from the episodic form and 10% from the chronic form. Based on functional neuroimaging central to the pathophysiology of the disease may be an abnormality in hypothalamic function that facilitate a cascade of metabolic and other biochemical events triggering an attack (see Cohen A S and Goadsby P J, "Functional neuroimaging of primary headache disorders" Expert Rev Neurother, 2006; 6(8):1159-1171). This sets off a positive feedback system involving the trigeminovascular system as the afferent limb and the parasympathetic outflow from the superior salivatory nucleus via the facial nerve through the SPG and OG as the efferent limb (see Goadsby P J, "Pathophysiology of cluster headache: a trigeminal autonomic cephalgia" Lancet Neurol. 2002; 1:251-57). Thus, vasodilatation of the pain-producing large cranial vessels and dura mater starts a reflex activation of parasympathetic vasodilator efferents which activate the trigeminal endings further to produce the excruciating pain and the parasympathetic symptoms (lacrimation and nasal congestion/secretion) seen in cluster headaches. In addition, the carotid swelling leads to a neuropraxic lesion of the sympathetic plexus surrounding the artery, resulting in a partial ipsilateral Horner's syndrome (ptose, miosis and conjunctival injection).

Current strategies for surgical treatment of these headaches include neurodestructive procedures targeting the trigeminal system (afferent limb) and the SPG (efferent limb), and neurostimulating procedures targeting the great occipital nerve and grey matter of hypothalamus (deep brain stimulation, DBS). Thus, cranial autonomic ganglia, and especially SPG and OG, are thought to have a role in the development of primary headaches and treatments have been established targeting the SPG.

Primary headaches may be hard to treat and the need for preventive treatments is enormous. Apart from CGRP antagonism, inhibition of the NO pathway may be considered the best documented and most promising target for treatment of primary headache (as described by Olesen J. in the reference above).

The trigeminal nerve is involved in all types of headache, including secondary headaches, i.e. headaches caused by other pathologies.

Sinonasal polyposis is a chronic hyperplastic disease of the nasal mucosa and the paranasal sinuses. There is a well established association between polyposis and rhinitis. The causes underlying the association could be due to chronic inflammation most likely induced by unstable autonomous nerve control of nasal vasomotor activity. This may precede the occurrence of nasal polyps. Vasomotor rhinitis seems to be related to an imbalance in the cranial autonomic system between parasympathetic and sympathetic activity. Therapies include vidianectomi and other forms of autonomic denervation which blocks parasympathetic activity through the SPG. Vidianectomi and other forms of autonomic denervation have also been an option for treating allergic rhinitis and new modified surgical techniques yield optimistic results.

Blocking the parasympathetic activity passing through the SPG by vidian neurectomy has shown to be effective in allergic rhinitis (see Wan-Fu S U, Shao-Cheng Liu, Feng-Shiang Chiu and Chia-Hsuan Lee. Antegrade transsphenoidal vidian neurectomy: Short-term surgical outcome analysis. Am J Rhinol Allergy 2011; 25:e217-e220), vasomotor rhinitis and rhinosinusitis with polyposis (see Cassano M, Mariano G, Russo L, Cassano P. Sphenopalatine artery ligation with nerve resection in patients with vasomotor rhinitis and polyposis: a prospective, randomized, double-blind investigation. Acta Oto-Laryngologica 2012; 132(5): 525-32).

Almost all patients who undergo parotidectomy will to some extent develop Frey syndrome (auriculotemporal syndrome or gustatory sweating) after surgery, because of aberrant regeneration of cut parasympathetic fibres between otic ganglion and subcutaneous vessels. Frey syndrome may also occur after extirpation of the submandibular gland, mandibular condylar fracture, and obstetric trauma caused by forceps. Nontraumatic causes are sympathectomy, autonomic neuropathy in diabetes mellitus, herpes zoster infection, and metabolic diseases. Frey syndrome may cause considerable social embarrassment and social incapacity due to profuse flushing and sweating when eating. Blocking the parasympathetic activity through the OG may constitute an effective treatment for these patients.

The cranial autonomic ganglia, and especially the SPG and the OG, are hence interesting targets for treating such entities, but they are not easily reached for interventions such as infiltration with pharmacological substances, destructive procedures or neuromodulation.

There are four paired cranial parasympathetic ganglia: sphenopalatine (pterygopalatine) ganglion (SPG), otic ganglion (OG), ciliary ganglion, and submandibular ganglion.

The SPG is pyramid shaped with a mean diameter of 3.5 mm. It is suspended from the maxillary nerve by the sphenopalatine nerves. Preganglionic parasympathetic fibres form the nervus intermedius of the facial nerve synapse with postganglionic fibres innervating the lacrimal gland, mucosa of the sinonasal cavity and cerebral blood vessels. Postganglionic sympathetic fibres from the superior cervical ganglion pass through the ganglion as well as sensory nerves from the maxillary nerve that innervates the palate and the epipharynx. The SPG can be identified using MRI.

The SPG is situated in the sphenopalatine (pterygopalatine) fossa (SF) and has the shape of a funnel flattened in the coronal plane. It is wider superiorly and then narrows down inferiorly with the apex pointing downwards into the greater palatine canal. SF has the following boundaries; superiorly with the infraorbital fissure, laterally with the pterygomaxillary fissure, medially with the palatine bone, posteriorly with the pterygoid plates, anteriorly with the posterior wall of the maxillary sinus and inferiorly with the palatine canal. Additionally, it communicates with the nasal cavity through the sphenopalatine foramen and the middle cranial fossa through the vidian canal and foramen rotundum. It can be divided in three compartments, an anterior compartment containing mainly blood vessels, a middle compartment containing mainly adipose tissue, and a posterior compartment containing mainly neural structures.

The maxillary artery enters the SF through the pterygomaxillary fissure and branches into the sphenopalatine artery, descending palatine artery, infraorbital artery, alveolar arteries and the artery of the pterygoid canal. The SF is often devoid of endoscopic identifiable veins. Blood vessels of the SF are tightly packed as they loop the anterior compartment and therefore a lateromedial intervention is more likely to cause a bleeding than an anteroposterior approach.

The average distance from the SPG to the vidian canal is 2.7 mm, to the infraorbital fissure 20.3 mm and to foramen rotundum 4.7 mm. It is normally located in the same vertical and horizontal plane as the vidian canal and posteriorly for the sphenopalatine foramen. The sphenopalatine foramen is vertically orientated located in the superomedial corner of SF with a diameter of 5-6 mm and typically located below the posterior end of the line of attachment of the middle turbinate and crista ethmoidalis, but this may vary. The average distance from the piriform aperture is 48 mm with an angle of elevation from the nasal floor is 22 degrees.

Such information of the distances from SPG to landmark identifiable on CT may be used to mark the SPG for image-guided interventions when MRI is contraindicated or not available.

OG is an oval structure measuring approximately 4 mm×3 mm×1.5 mm. It is composed of parasympathetic fibres arising in the inferior salivatory nucleus in the medulla, sympathetic fibres form the superior cervical sympathetic ganglion, and motor fibres from the mandibular branch of the trigeminal nerve. The OG supplies secretory fibres to the parotid gland and parasympathetic fibre to cerebral blood vessels. It is situated just posterior of the lateral pterygoid plate below the foramen ovale in the infratemporal fossa and adjacent to the middle meningeal artery, mandibular nerve and buccal nerve.

For minimally invasive interventions in the SF there are three surgical approaches, each with its advantages and disadvantages; a lateral approach through the pterygomaxillary fissure, a medial transnasal approach through the sphenopalatine foramen and a transoral approach through the greater palatine canal. All approaches give a relatively easy access to SF for someone skilled to the art, but there are pivotal differences if a high-precision intervention in the closest proximity of the SPG is needed.

Image guided surgery (IGS) was developed to improve accuracy and precision. Such technology is used to assist in orientation by displaying the position of a pointer or surgical instrument on a medical image. Armless systems may be based on light, sound waves or magnetic fields. With the use of a computer platform, a tracking system and a body marker, a pointer or other instrument can be calibrated so that the navigation system will display the tip of the instrument correctly. The instruments are calibrated in advance by the manufacturer or the surgeon may use a universal instrument integration system to calibrate basically any instrument. This system is based on a set of universal clamps attached to the instrument. There are several limitations to this solution. Firstly, attaching the clamps can be challenging and they can easily move, hence giving a wrong impression of the actual localization of the instrument on the medical image. Secondly, semi-rigid instruments are not suitable for calibration because they can bend after calibration, such as e.g. a thin needle or a long forceps.

The lateral approach is typically carried out under local anaesthesia. Typically a high-precision intervention would be an infrazygomatic approach. Using the infrazygomatic approach there is a straight line through soft tissue from the skin to the SF, SPG, orbita and the sphenopalatine foramen. The distance from the skin to the SF or the SPG is approximately 6-9 cm making it next to impossible to achieve a high precision infiltration without the use of IGS. Violating the sphenopalatine foramen could result in a complicated posterior epistaxis, violating the infraorbital fissure could damage intraorbital tissue. Using the suprazygomatic approach, which is described in U.S. Pat. No. 7,981,433, for example, the sphenoid bone will normally obstruct access to the SF and in particular the middle and the posterior compartment and almost always obstruct access to the SPG, making it quite safe, but not applicable for high-precision interventions. If anatomical variations enable advancing a needle to the close proximity of the SPG by a suprazygomatic approach, it would be next to impossible to successfully target such a small structure with a conventional injection technique as described in U.S. Pat. No. 7,981,433. Due to the low diffusion rate of botulinum toxin and the fact that the SF mainly contains adipose tissue, a hydrophilic substance injected using these techniques will rarely reach its target.

The medial transnasal approach is difficult to perform under local anaesthesia due to the sensible posterior region of the nasal cavity, and the use of general anaesthesia makes it much less accessible. Due to the complex sinonasal anatomy it is normally performed by a rhinologist. For someone skilled in the art this approach is the most accurate, mainly due to the low distance between the puncture site and the SPG. Normally such an approach is done by advancing the needle through the sphenopalatine foramen, risking damage to the sphenopalatine artery/arteries. The palatine bone, which constitutes the anterior border of the sphenopalatine foramen, is quite thin, and a suitable needle can quite easily be advanced through the bone, avoiding possible damage to the sphenopalatine artery.

However, such a procedure can easily bend the needle used, which will generally be an 18 G needle or thinner. After it has been advanced through the bone the end of the needle is in the soft tissue and there is no way to know if deformation has occurred or to what extent, making the intervention unsafe and imprecise, with the use of IGS or not. For injections in deep tissue a 25 G needle or thinner is recommended to avoid unnecessary tissue damage, including bleedings and nerve damage. Furthermore, the thicker the needle the bigger the dead space, which hinders use of small injection volumes. As a consequence of these issues, needles suitable for SPG injection using the medial approach and also other approaches are not suitable for high-precision injections.

The transoral approach can be done with local anaesthesia. However, due to the direction of the palatine canal towards the very anterior part of the SF, high-precision interventions targeting the SPG are not feasible with this approach.

Intervention targeting the OG can be done via a lateral approach as described in interventions targeting the trigeminal ganglion through the oval foramen, or lateral approaches with the same injection sites as described above, i.e. infrazygomatic or suprazygomatic. It is also possible to apply a transnasal medial approach through the maxillary ostium and the posterior wall of the maxillary sinus and advancing adjacent to the lateral pterygoid plate. With this transnasal medial approach one can avoid important nerves and blood vessels in the infratemporal fossa and was performed without complications or side effects. This medial approach seems as well appropriate for neurostimulators as it can be situated and anchored to the pterygoid plate.

The cranial parasympathetic ganglia including the SPG and OG are surrounded by critical neural structures and organs like e.g. brain and eyes. Drug impact of these structures can cause serious complications and should be avoided. In addition, some medications diffuse slowly and they must be injected with millimeter accuracy to reach their target. As a result, accuracy is important in various situations:

1) When using a drug or implant that only works exactly where it is injected/situated.

2) Use of a diffusible drug that must be injected at a safe distance from sensitive structures (e.g. brain or eye).

3) When using a drug or implant that can cause serious complications if it is injected accidentally in the wrong place.

4) For injection into an area where the needle can damage other nearby structures.

All four factors are important when it comes to injections of botulinum toxins (as known by the trade name Botox, for example) or similar neurotoxins to the SPG or OG, and some or all of the factors also apply to other medications that one can envisage using in blocking of cranial parasympathetic ganglia. Moreover, since the same or similar requirements arise in many other situations requiring delivery or a substance or insertion of an instrument to a targeted site within the human or animal body then a device and/or method capable of addressing the need for targeting of the cranial parasympathetic ganglia will have numerous other uses and advantages.

As noted above, prior art such as U.S. Pat. No. 7,981,433 discloses administration (topical and by injections) of neurotoxins (e.g. Botox) to parasympathetic (including SPG), trigeminal and occipital nerves in the treatment of headaches, amongst other things.

U.S. Pat. No. 7,981,433 describes an injection technique, specifically a lateral approach, which is a conventional suprazygomatic approach. This approach makes it impossible to accurately deposit substances, since the sphenoid bone will normally obstruct access to the SF and in particular the middle and the posterior compartment and almost always obstruct access to the SPG, making it quite safe, but not applicable for high-precision interventions. Due to the low diffusion rate of botulinum toxin and that the SF mainly contains adipose tissue, a hydrophilic substance will rarely reach its target. There is no consideration in U.S. Pat. No. 7,981,433 of the techniques required to reach other parasympathetic ganglia (most importantly the OG). Thus, there is a significant unmet need for a safe, high-precision system for targeting of cranial parasympathetic ganglia and other similar target sites in the human or animal body.

Viewed from a first aspect, this disclosure provides a device for interventions within the body, the device comprising: an end piece for insertion into the body at a distal end thereof, the end piece including a rigid lumen for holding an instrument and guiding the instrument to the distal end of the end piece; and a body section supporting the lumen and being rigidly connected thereto, the body section including a navigation array for guidance of the device using a surgical navigation system and/or including an anchor point for a standard navigation array.

The device hence includes a rigid lumen for guiding an instrument, such as a needle for example, and delivering it to a point within the body, this lumen being provided in combination with the ability to work with a surgical navigation system to enable the device to accurately target of a location in the body, for example cranial parasympathetic ganglia as discussed above. Whilst navigation arrays are available with clamp type connections that purport to join to any instrument these do not provide a reliable rigid connection and hence movement between the navigation array and instrument leads to inaccuracies. Further, even if it were possible to guarantee accuracy then in the absence of the rigid lumen deformation of the instrument could occur, once again leaving to lack of accuracy. As explained above accurate positioning of the instrument is of paramount importance and without the use of a device that is both rigid and navigable maximum accuracy cannot be obtained.

The distal end of the end piece is the end that is located in the body when in use, with a proximal end of the end piece joining to the body section. The distal end of the end piece may comprise a tip for piercing the body. The tip preferably has a tapered profile narrowing toward a point so that it can easily penetrate body tissues and bone, if transition through body tissue and/or bone is necessary for the selected approach to the desired target site. The end piece may comprise a scale or other marking to show the depth of insertion into the body.

The lumen should be rigid enough to permit placement of a tip of the end piece with millimeter accuracy without deformation as the lumen penetrates the intervening body tissues, or navigates through an open cavity such as the nasal cavity, and whilst being subject to bending moments that might arise as it is manoeuvred along the selected approach toward the target site, for example the SPG or the OG. For injections towards the SPG an end piece for the medial approach would need to be more rigid than for the lateral approach due to the need for penetration of bone and for a longer end piece. In a preferred embodiment the device is intended for targeting the SPG or the OG via a lateral approach and the lumen has a rigidity sufficient to limit deflection of the end piece and/or lumen as it advances along that lateral approach to a maximum of 3 mm per 10 cm of length of the needle, preferably a maximum of 2 mm per 10 cm and more preferably 1.5 mm per 10 cm.

Suitable end pieces may have an internal diameter in the range 0.7 to 1.8 mm and a wall thickness of at least 0.05 mm, in some embodiments at least 0.1 mm. Typically the end piece will have a tapered outer diameter, getting thinner toward the distal end. The tapering may have any suitable profile, and in preferred embodiments the end piece will have a region of constant outer diameter at the proximal end, with a tapering region at the distal end. Generally the internal diameter will be constant throughout the end piece. With a tapered outer diameter and constant inner diameter the wall thickness at the proximal end will be larger than the minimum wall thickness, which will be at the distal end. The wall thickness at the proximal end may be at least 0.5 mm, in some embodiments at least 0.75 mm. Typical outer diameters at the proximal end may be in the range 2-4 mm, for example around 3 mm.

A preferred material for the end piece, which will provide the required rigidity with the dimensions mentioned above, is beta titanium. Stainless steel is another possible material.

In general the end piece and/or lumen may be made as rigid as the standard for commercially available navigable instruments on the market. The end piece and/or lumen may have a rigidity that is at least 60% of the rigidity of the instrument sold under the name VectorVision™ Pointer, with blunt end, as supplied by BrainLAB AG of Germany, the rigidity being as measured during a deflection test with the lumen/instrument being supported in cantilever fashion and a load being applied at the tip. The rigidity may be equivalent to or greater than that of the VectorVision™ Pointer.

The navigation array may comprise optical markers or electromagnetic location sensors, for example optical reflectors such as reflector balls or electromagnetic coils. Any suitable navigation array system can be used. The navigation array may comprise a plurality of markers located in plane with one another and at known locations relative to the end piece. In one preferred embodiment there are at least three markers, for example there may be four or five markers. The navigation array should be rigidly connected to the body section and hence rigidly connected to the end piece. The end piece may have a known orientation and size relative to the navigation array, or a calibration sequence may be performed to provide appropriate data concerning the orientation and size of the end piece relative to the navigation array. A rigid and integrated connection of the navigation array with the body section is preferred since this provides the least risk of inaccuracy and inadvertent misalignment of the navigation system with the end piece. Alternatively, when an anchor point is provided then the anchor point should be arranged for rigid connection of the navigation array to the body section. The anchor point may, for example, be for connection to an array of the type supplied under the trade names SureTrack® Universal tracker from Medtronic and Brainlab Instrument Adapter System from Brainlab.

In preferred embodiments the navigation array is held in a track on the body section that permits slidable movement relative to the body section, and the navigation array is rigidly connected to the instrument. The array is hence rigidly fixed to the instrument, whilst both the array and the instrument can move relative to the end piece and body section of the device. This means that as the instrument is advanced or retracted through the lumen then the navigation array will remain in the same position relative to the instrument. Guidance of the instrument can be simpler with this approach, and advantageously it facilitates use of the device as a dynamic pointer. For example the instrument could be a rod, which can be placed close to a target site in the body using the rigid lumen, and then advanced more closely to the body without the need to further move the main parts of the device. With this feature the device may also have the capability to lock the navigation array in place in the track in order to permit use in an alternate mode with the navigation array being used to monitor movement of the end piece and the location of the instrument being monitored either by additional navigation devices or by a scale on the device.

Preferably the device comprises a proximal piece for holding a proximal end of the instrument. The proximal piece may be positioned at a proximal end of the end piece and may be connected to the end piece either directly or via the body section. The proximal piece may be mounted to the body section at an opposite end of the body section to the end piece. It is preferred for the proximal piece to comprise parts that are moveable relative to the end piece and are for fixed connection to the instrument. Such parts can be used in the manipulation of the instrument as described below.

In a particularly preferred embodiment the proximal piece comprises one or more clamp(s) for attachment of the instrument. A clamp or clamps may advantageously be provided on the proximal piece to fix the instrument in place relative to the end piece and the distal end thereof.

When the device has been inserted into the body to a suitable point with reference to a target site the instrument can be operated by manipulation of the proximal end of the instrument at the proximal piece. For example, the instrument may be extended from the distal end of the end piece to move it closer to the target site. When the instrument is a needle this allows for highly accurate targeted injection without the risk of damaging the target site with the rigid and larger diameter end piece. A scale is preferably provided on the proximal piece in order to show the movement of the instrument, for example how far the instrument has been inserted.

The proximal piece may comprise two clamps for releasable connection to the instrument, with one clamp slidable relative to the scale and hence useable to indicate movement of the instrument. Alternatively, or in addition, the proximal piece may comprise positional markers, e.g. in the case of an optical system, reflectors, for indicating the distance. For example, a positional marker may slide along the proximal piece connected to an associated one of the clamps, which in turn may be for fixed connection to the instrument during use, so that the positional marker moves along with the instrument. In a preferred embodiment the proximal piece includes a handle, such as a ring piece, for enabling the user to push or pull the instrument with the thumb or a finger.

The moveable parts of the proximal piece, which are for connection to the instrument, may advantageously be connected to the navigation array when the navigation array is held in a track on the body section as described above. Thus, the rigid connection of the navigation array to the instrument may be via a coupling between the moving parts of the proximal piece and the navigation array.

The device may include a cheek-stopper to prevent the instrument from being advanced too far into the body.

Advantageously, the device can be used in relation to a target site at any region of the body. The rigid end piece can guide a less rigid instrument toward the target site in a highly accurate and navigable manner irrespective of the type of instrument or the location of the target site. In some preferred embodiments the device is for cranial use, for example for targeting of the SPG or other of the cranial parasympathetic ganglia, for example the OG. The device may hence include a lumen and end piece with sufficient rigidity to advance easily along the selected approach, which in preferred embodiments is the lateral approach to the ganglion of interest. For example the rigidity may be sufficient to limit deflection of the end piece and/or lumen as it advances along the lateral approach to a maximum of 2 mm per 10 cm or other deflection value as discussed above. As noted above, this rigidity may be at least 60% of the rigidity of the instrument sold under the name VectorVision™ Pointer, with blunt end, as supplied by BrainLAB AG of Germany.

The end piece may have a tip adapted to bend the instrument as it is pushed through the lumen and out of the tip. For example, the tip may be an angled tip and/or the tip may comprise internal contours within the end of the tip to angulate the needle as it exits a hole at the very end of the tip or as it exits a hole in the side of the tip. A tip angled at 45 degrees may be used for a device intended for the medial transnasal approach to the SPG, since this enables the device to direct a needle or other instrument closest to the SPG. It may be preferred to use internal contours since in comparison to an angled tip there is no additional disruption to body tissue as the end piece is inserted into the body.

The device can advantageously be used with any instrument capable of passing through the lumen. In preferred embodiments, where the device is for injection of substances into the body, the end piece is for receiving and guiding a needle. For some embodiments the lumen is designed to receive an 18 G needle or smaller, more preferably a 25 G needle or smaller. The needle may be included as a part of the claimed device.

A preferred needle is provided with a needle tip having a slightly rounded end. This acts to minimise the risk of damage to the target site. The needle preferably comprises openings on each side of the tip rather than at the tip end. This means that tissue on either side is infiltrated by the injected pharmacological substance, and additionally decreases the risk for injection of a substance directly into the ganglion. The proximal end of the needle, or some intermediate point of the needle, for example at the body section, may be provided with a luer lock device for connection to an appropriate source of the pharmacological substance.

In a preferred embodiment a vessel such as an ampule or syringe is attached to the needle at the body section or at the proximal piece. With the ampule feature the device may be provided with a locking mechanism to lock the proximal piece and/or the instrument in position, for example using a first lever or actuator, and a second mechanism to aspirate and then inject a substance from the ampule, for example using a second lever or actuator, advantageously there may be two levers of different lengths for ease of operation.

The instrument may be a pointer, for example a blunt ended rod. A pointer is used to point at and identify structures during a procedure in an open cavity, such as the paranasal sinuses or nasal cavity. Known pointers have a fixed length. While using such pointer it is normally quite difficult to use an endoscope simultaneously since the view can be blocked and the pointer and endoscope can collide. By using a rod as a working instrument, preferably a rod connected to the proximal piece of the device, the device may be used as pointer. Such a pointer has the advantage that the rod/pointer can be moved, without moving the main body of the device, which minimises the possibility of colliding with other instruments.

In one preferred arrangement an endoscope is attached to the device, for example the endoscope may be attached to the body section and directed along the line of the end piece. This means that any movement in any direction will not cause a collision between the device and the endoscope, making the device very user friendly especially when used as a pointer.

A display screen may be attached to the device. This enables endoscopic images and/or navigation images to be shown easily to the user of the device and the images can be aligned with the orientation of the end piece. One possibility is for a handheld device, such as a smart phone or tablet computer, to be attached to the body section or another part of the intervention device. The handheld device may be mounted in an appropriate cradle. A further optional feature is for the handheld device to include a camera and software for automatic recognition of features of the end piece, for example by reference to the length and/or curvature of the end piece. This software may be linked with or form a part of the guidance software.

The instrument may be a neurostimulator such as a neuromodulator. With this feature the neurostimulator may sit at the tip of the device so that the device can be used to implant it at the target location the body. The neurostimulator may comprise a lead passing along the lumen from the tip toward and/or to the proximal section, whereby the lead can be anchored within the body, with or without a neurostimulator also positioned within the body, and the lead left in place providing an electrical connection into the body when the end piece is withdrawn and the device removed from the body. Alternatively the neurostimulator may be arranged to activate in response to induced electric current when it is exposed to a suitable electromagnetic field.

The neurostimulator preferably includes a coupling for attaching to the body at the target location, for example at a point close to the SPG. In preferred embodiments the neurostimulator is detachably connected to the tip such that after coupling to the body the neurostimulator will disengage from the device as the end piece is withdrawn from the body.

The neurostimulator may be included as a part of the claimed device. One possible neurostimulator design is that currently supplied under the trade name ATI Neurostimulation System by Autonomic Technologies, Inc of Redwood City, Calif., USA as described at http://www.ati-spg.com/europe/en/therapy/ati-system/. Another possible neurostimulator is the Ischemic Stroke System as supplied by BrainsGate of Israel.

The instrument may comprise an implant such as a steroid implant or a drug eluting stent. Steroid implants and drug eluting stents are used for treating sinusitis, and post-operatively to avoid recurrence. Such devices are normally implanted in the ethmoidal sinuses. The implantation technique may in certain cases be quite difficult due to local anatomy. It is described in the literature serious complications due to unintentional insertion in the orbit. Such implants may be implanted by means of the device described herein in a safer manner than the prior art techniques. For example, an end piece with its distal end arranged to hold the implant and a rod connected to the proximal piece to push the implant out, will allow safe insertion the implant.

The instrument may also be a needle for core needle biopsy, a needle for fine needle biopsy, an electrode for electric or radiofrequency ablation therapy or a cannula for chemical ablative therapy.

Viewed from a second aspect, this disclosure provides a method of use of the device of the first aspect comprising: inserting the device into the body and using a navigation system to guide the end piece toward a target site within the body, the navigation system being associated with the navigation array of the device or with a navigation array attached to the anchor point of the device.

The device used in this method may have features as described in relation to the preferred features of the first aspect. The method may comprise use of a needle as the instrument and injection of a pharmacological substance into the body at a target site.

In one preferred embodiment the method may comprise navigated insertion of the end piece of the device toward the SPG along the lateral approach described herein. In the pre-operative planning a standard IGS planning station (e.g. iPlan by Brainlab) may be used to define the best choice of approach (where there is a straight line through soft tissue towards the SPG).

The method may be for treating or preventing headache in a patient such as a human in need thereof and may comprise injecting a neuroinhibitory substance such as botulinium toxin in close proximity (i.e. proximally) to the sphenopalatine ganglion or otic ganglion wherein an injection device comprising said neuroinhibitory substance is brought into close proximity to the sphenopalatine ganglion or otic ganglion by inserting said injection device into the patient transnasally or infrazygomatically and the neuroinhibitory substance injected in close proximity to the SPG or OG.

The method may be for treating or preventing rhinitis, rhinosinusitis, Frey syndrome or hypersecretion of tears in a patient such as a human in need thereof and may comprise injecting a neuroinhibitory substance such as botulinium toxin in close proximity to the sphenopalatine ganglion or otic ganglion wherein an injection device comprising said neuroinhibitory substance is brought into close proximity to the sphenopalatine ganglion or otic ganglion by inserting said injection device into the patient transnasally or infrazygomatically and the neuroinhibitory substance injected in close proximity to the SPG or OG.

Viewed from a further aspect, this disclosure provides a computer programme product containing instructions that when executed with configure an image guided surgery navigation system to guide the end piece of the device described above toward a target site within the body. In a preferred embodiment, the computer programme product configures the image guided surgery navigation system to guide the end piece toward the sphenopalatine ganglion (SPG) along a lateral approach.

Certain preferred embodiments will now be described by way of example only and with reference to the accompanying drawings in which:

FIG. 1 shows an example of an intervention device in side view;

FIG. 2 is a detail view showing features of a needle used with the intervention device of FIG. 1;

FIG. 3 shows arrangements for the tip of the intervention device of FIG. 1;

Figure 10A:
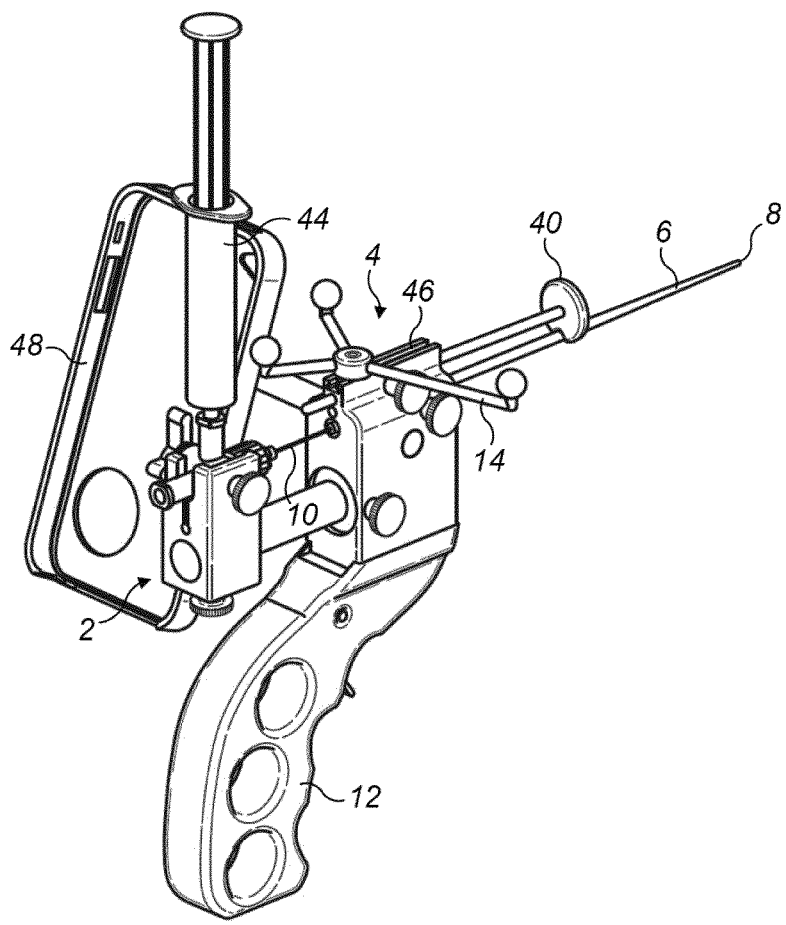
Figure 11A:
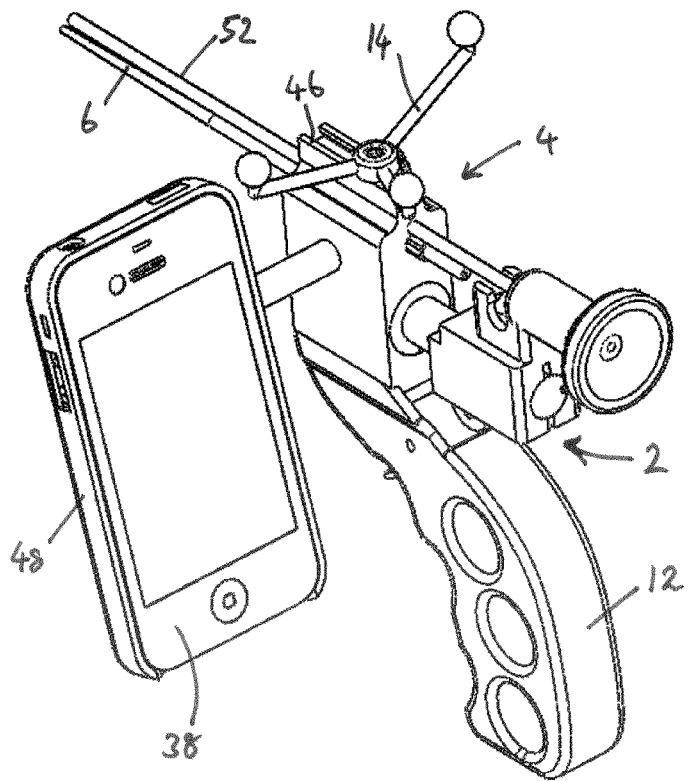
Figure 11B:
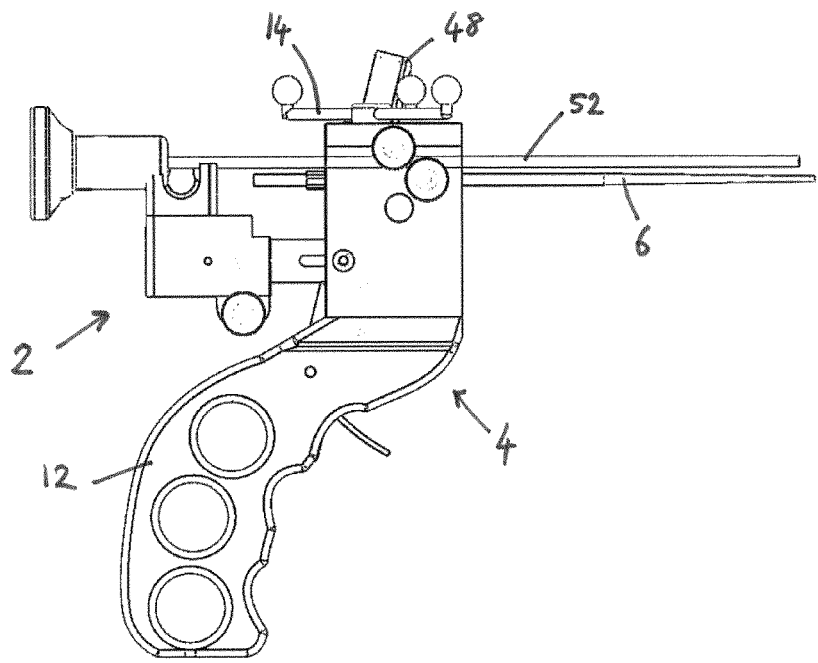
Figure 12:
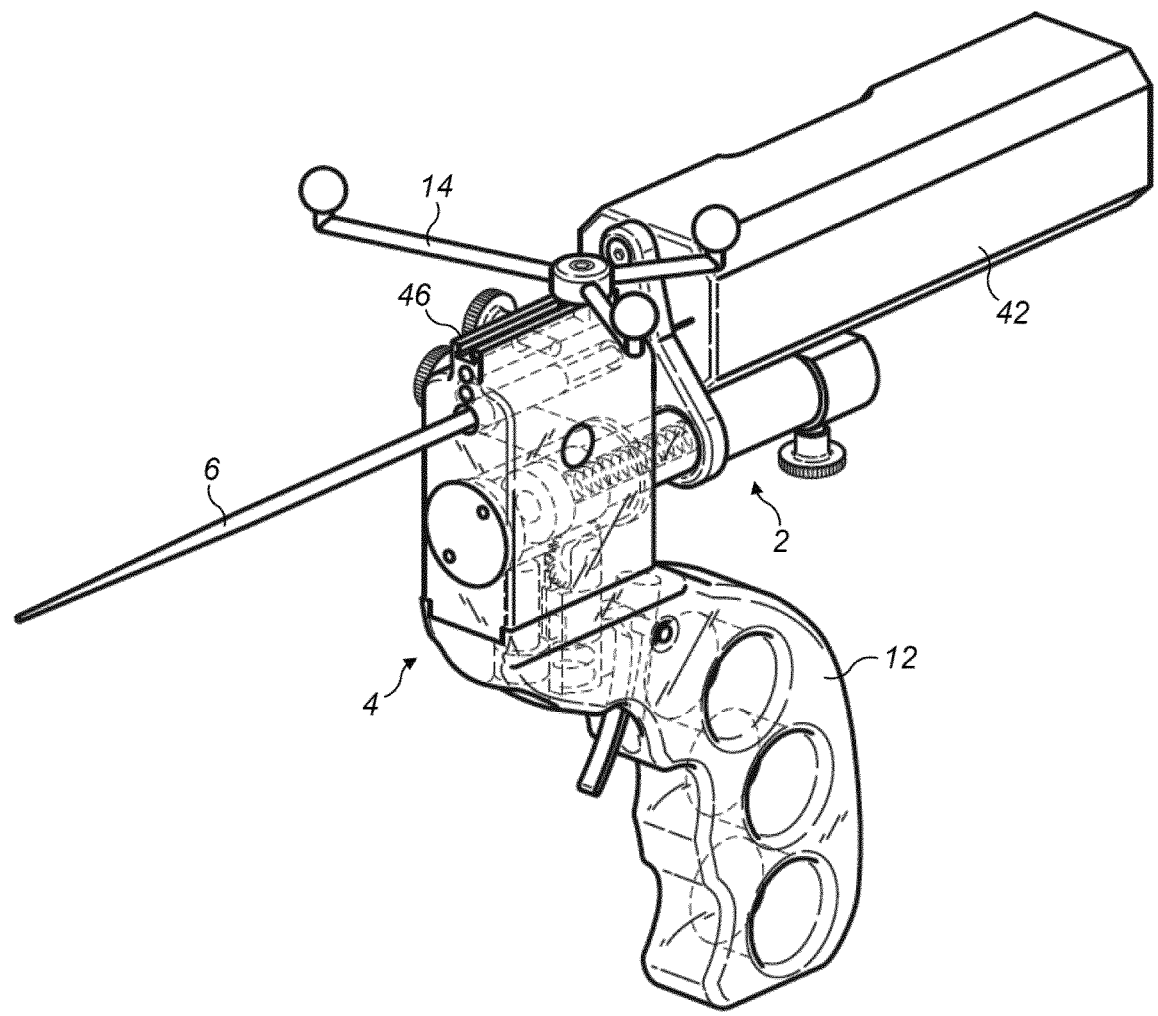
Figures 13A, 13B:
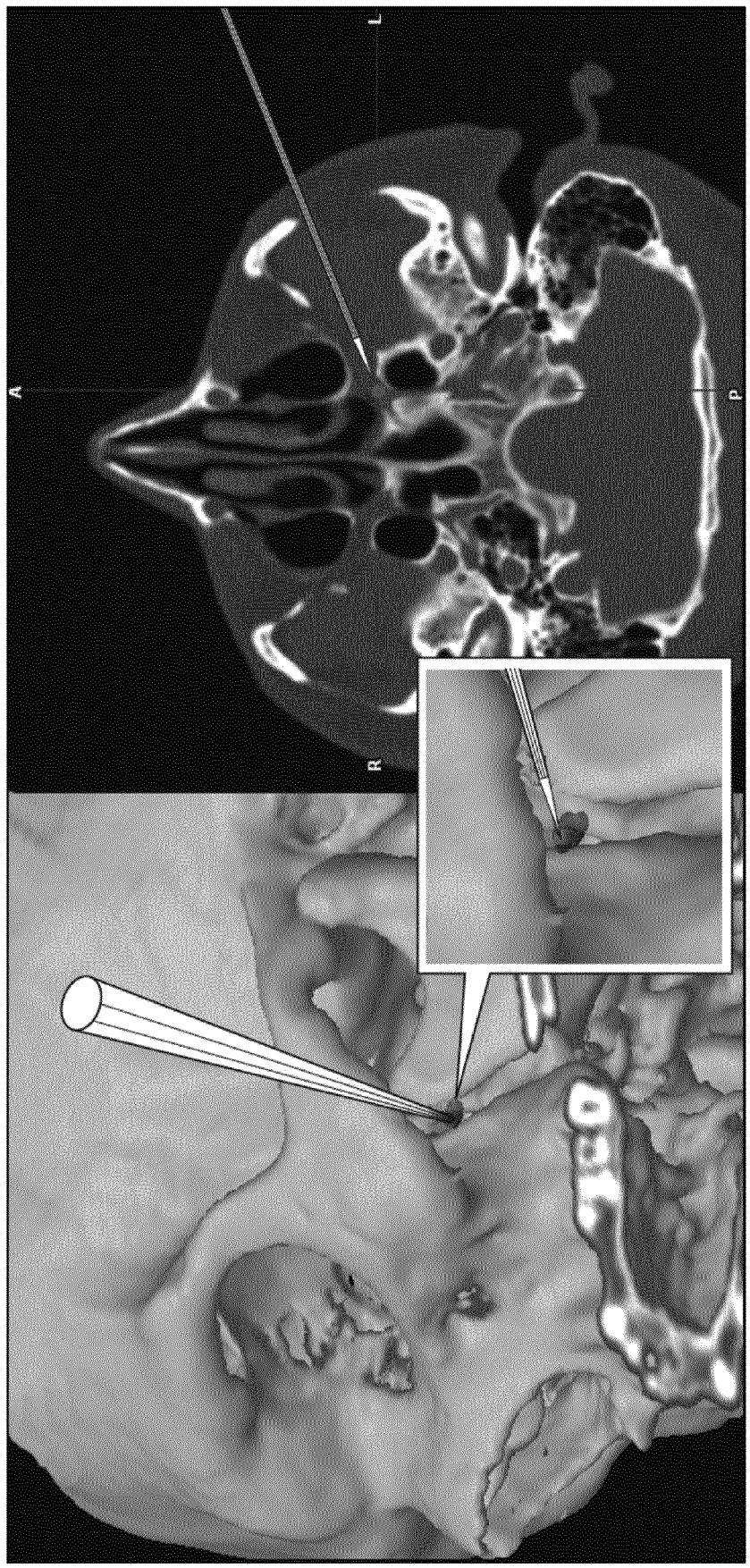
Figure 14:
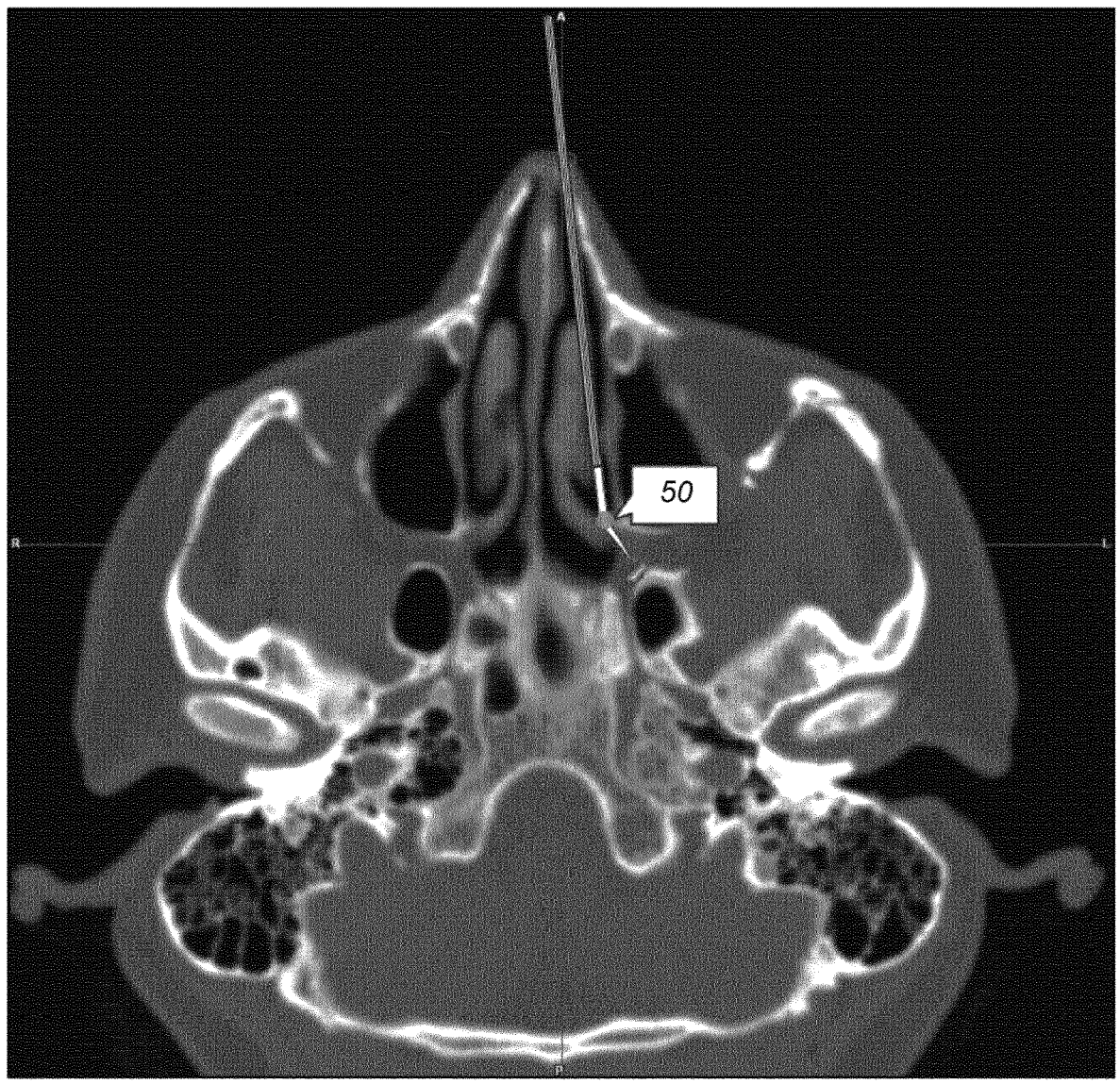
Figure 15B:
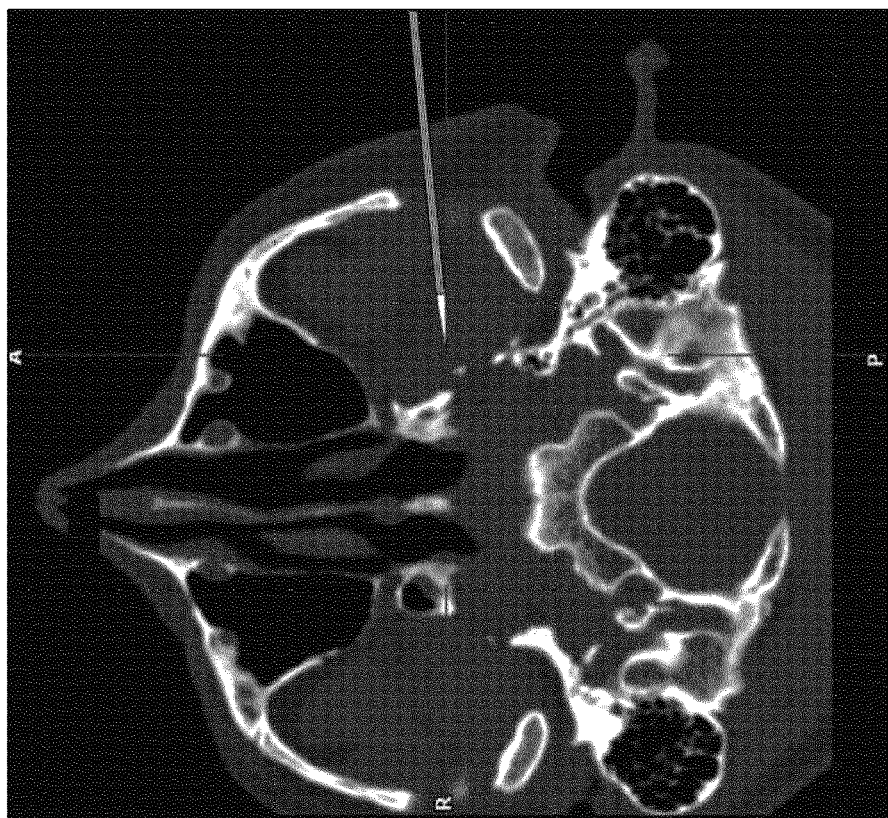
Figure 15A:
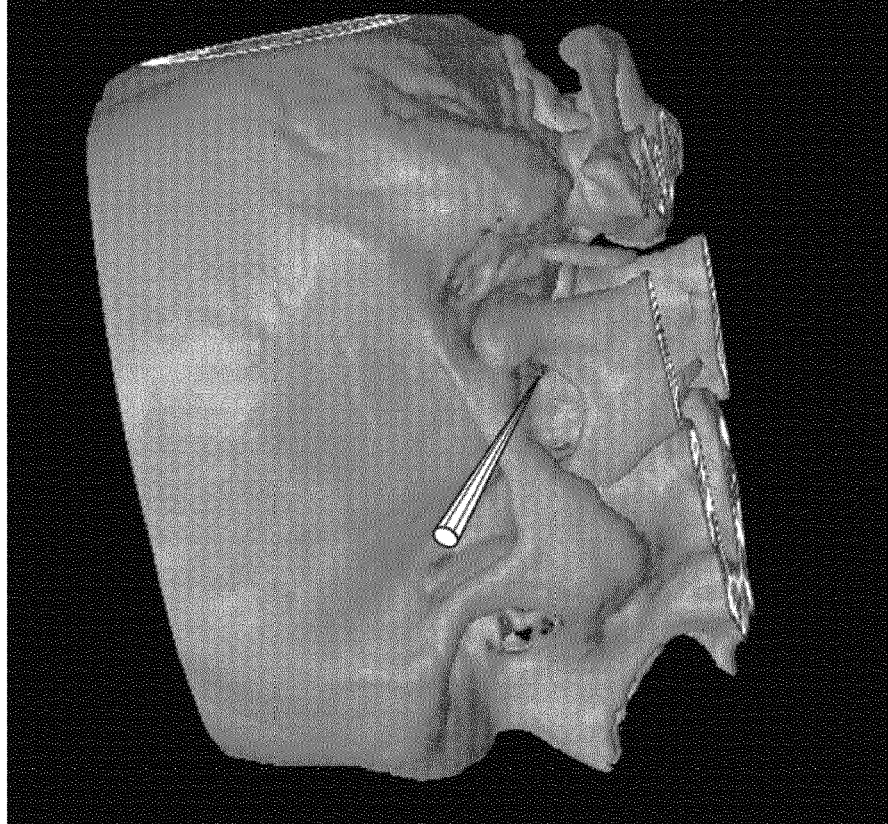

FIGS. 10a and b show a further example of an intervention device including an optional cradle for a handheld device and an optional cheek stopper;

FIGS. 11a and 11b show another example, wherein the intervention device is fitted with an endoscope and smart phone;

FIG. 12 is a perspective view of a still further example of an intervention device;

FIGS. 12a and b show the location of the SPG in the head with the device shown approaching the SPG infrazygomatically;

FIG. 14 shows the transnasal approach with a device having an angled tip, wherein the end piece passes through the nasal cavity and therefore only penetrates the mucosa at the shown point;

FIGS. 15a and b show the infrazygomatic approach to the OG; and

Figure 16:
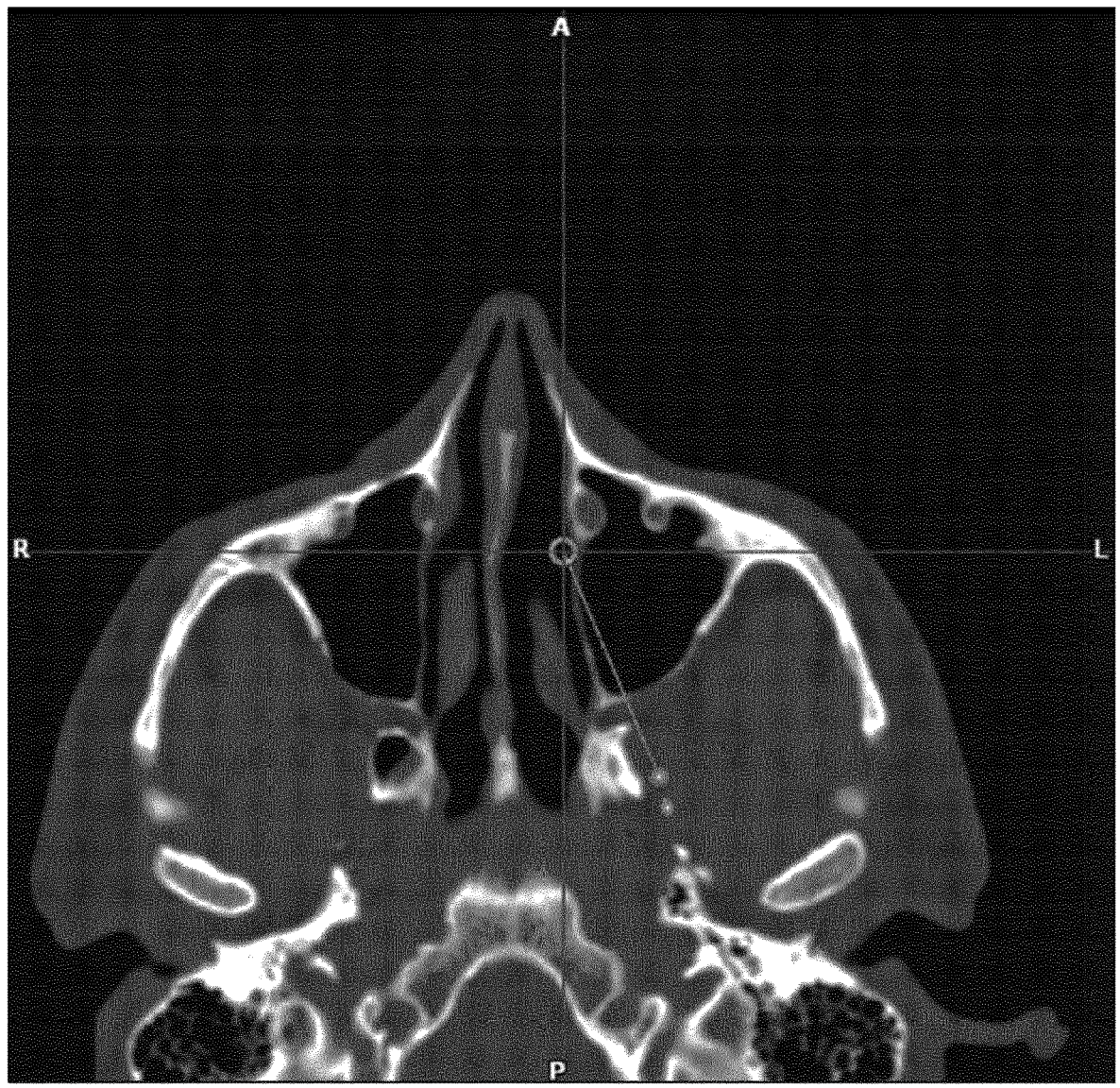

FIG. 16 shows the transnasal approach to the OG, this approach being defined by a straight line.

FIG. 1 shows an intervention device for high-precision image guided interventions targeting cranial autonomic ganglia. The device can also be used wherever applicable for injections, core needle biopsy, fine needle biopsy, puncture, aspiration, ablation, and for the positioning of electrodes, radioactive seeds, catheters or implants.

The device consists of a proximal piece 2, body 4 and an end piece 6 with a tip 8. It is made of a rigid material to avoid navigation inaccuracy. This is of paramount importance since there is no way for the interventionist to be aware of deformations of an instrument as soon as skin or mucosa is punctured and the instrument is within the body.

The end piece 6 comprises a rigid lumen through which an object such as a needle 10 can pass. The lumen can be of any suitable diameter, length and form, provided that it has sufficient length to penetrate to the injection site. In this example embodiment it is sized for use in a lateral or transnasal medial approach to the SPG and hence the end piece 6 extends away from the body 4 by about 12 cm allowing for sufficient length to penetrate the skin and reach the SPG, which can be perhaps 6 to 9 cm from the skin as noted above. The lumen of the end piece 6 is made of a rigid material to avoid navigation inaccuracy and it should be rigid enough to permit placement of the tip 8 with millimeter accuracy without deformation as the lumen penetrates the intervening body tissues and whilst being subject to bending moments that might arise as it is manoeuvred along the selected approach toward the SPG (which may be transnasal or lateral). The lumen of this example has a diameter just big enough fit a 25 G needle with appropriate clearance.

The end piece 6 has centimeter marks to provide an indication of the depth of insertion beneath the skin. The end piece 6 extends through the body 4 and is attached to proximal piece 2 to allow for the needle 10 to extend along the proximal piece as described below. The lumen is open at the proximal end to provide access for the needle 10. The tip 8 can be sharp as shown or rounded to minimize tissue damage. Potential adaptations to the design of the tip 8 are discussed below in relation to FIG. 3. The outer diameter of the end piece 6 may taper off from the proximal end to the distal end of the end piece 6. The very distal end of the end piece may be approximately 20-22 G. The inner diameter will typically be just big enough to carry the preferred 25 G needle.

The body 4 is connected to and holds the end piece 6 and proximal piece 2. The body 4 includes an ergonomic shaped handle 12 that allows for one-handed use. The body 4 also holds an array 14 with reflector balls for an optical guidance system mounted on a suitable anchor point 16. This optical guidance array 14 can be used in conjunction with further reflector balls 18 mounted on the proximal piece for best accuracy and to permit the navigation system to also monitor the position of the needle 10 within the end piece 6. The body 4 in this example also has a universal clamp anchor point 20, which is formed to fit universal clamps as provided by manufacturers, and also an electromagnetic anchor 22. The various anchor points 16, 20, 22 allow for alternative guidance systems to be used for the needle guide. For electromagnetic navigations system any connection point provided by the manufacturer could be embedded.

The body 4 optionally includes a mounting point (for example, as described below in relation to FIGS. 5 to 7) for a handheld device replacing the traditional computer platform, such as a tablet, smart phone, iPod™ or the like. The display screen of the handheld device can be used during navigation to show the operator what movement of the end piece is required or to show images from an endoscope attached to the intervention device. Such a handheld device can include software that by animation (e.g. three-dimensional) of the medical image with targets and bars, will provide guidance to the operator in relation to the puncture site, alignment of the end piece and distance to the target along with warnings if the device is off track. The software may display a magnified view of a region of interest in the navigation image on the screen of the handheld device. Appropriate software could also be integrated into the software of the computer platform provided by the manufacturers of navigation systems either in addition to software on a handheld device and capable of interacting with the handheld device or as an alternative allowing the use of a separate computer platform without a handheld device. This can make the intervention procedure safer and more precise. Furthermore, it can make the procedure available not only for specialized surgeons but also to surgeons with less experience in this field as well as potentially to other medical professionals such as neurologists and anaesthesiologists. This is of importance since the ease of performing a procedure and hence its availability to patients is as important as the existence of such procedure. The handheld device can communicate with a computer platform through Wi-Fi, Bluetooth or the like. The computer platform can be integrated in a tracking rack, making it convenient for storage and transport, and therefore for outpatient use or the like. The device may include a sensor in the body of the device connected to the handheld device that registers movements of the needle and/or of the proximal piece, this is done with or without usage of the possibility of tracking movements by markers on the proximal piece.

The proximal piece 2 is attached to the end piece 6 and the body 4. The proximal piece comprises two clamps 24 for attachment of the needle 10. These clamps 24 are used to fix the needle 10 in place relative to the tip 8. With appropriate guidance from an optical navigation system or similar, the needle guide can be pushed forward using the tip 8 and end piece 6 to penetrate the skin and body tissue. When the tip 8 is at a suitable distance from the target site the distal end of the needle 10 can be extended from the tip 8 by manipulation of the proximal end of the needle 10 at the proximal piece. A scale provided on the proximal piece shows how far the needle has been inserted. In this way the device avoids the risk tissue damage that might otherwise be caused by the larger end piece of the device approaching close to the target site. Extending and then retracting the needle 10 can also be used to avoid backflow of a pharmacological substance as one retracts the device.

Another way to measure the distance that the needle 10 has been moved is the use of positional markers, e.g. in the case of an optical system, reflectors, for calculating the distance. In the embodiment shown one of the reflector balls 18 could slide along the proximal piece 2 connected to an associated clamp 24 and hence provide an indication of the distance that the needle 10 has moved. In such cases, with appropriate software, the position of the needle can be seen on a navigation screen or other computer device.

The device will be made of a rigid material to avoid IGS inaccuracies. Any instrument guided by the device can be semi-rigid, in this case the needle 10, as the device in itself provides the requisite stiffness to ensure that the intervention is accurate.

The needle 10 in this example is a 25 G needle that is provided with a specially designed needle tip 26, which is shown in FIG. 2. The tip 26 has a slightly rounded end to minimise the risk of damage to the target site (the SPG in one example) and there are openings on each side of the tip 26 so that tissue on either side is infiltrated by the pharmacological substance. FIG. 2 also shows detail of the proximal end of the needle 10, which is provided with a luer lock device for connection to an appropriate source of the pharmacological substance, for example a syringe.

FIG. 3 shows potential alternative designs for the tip 8 of the lumen, with adaptations to bend the needle 10 as it is pushed out of the tip 8 and to thereby direct it away from the line of the end piece 6. This allows for targeting of injection sites that are not in a location than can be easily accessed in a straight line from an appropriate puncture site. Since the effect of the shaped tip 8 on the final position of the needle 10 as it is extended will be known then the angled path of the needle 10 can be taken into account when the desired path for insertion of the end piece 6 into the body is determined. FIG. 3 shows three possible arrangements, including an angled tip 8, and two systems using internal contours within the tip 8 to angulate the needle 10 either as it exits a hole at the very end of the tip 8 or as it exits a hole in the side of the tip. One advantageous use for an angled tip 8 is shown in FIG. 11, where the SPG is targeted using a transnasal approach.

Figure 4:
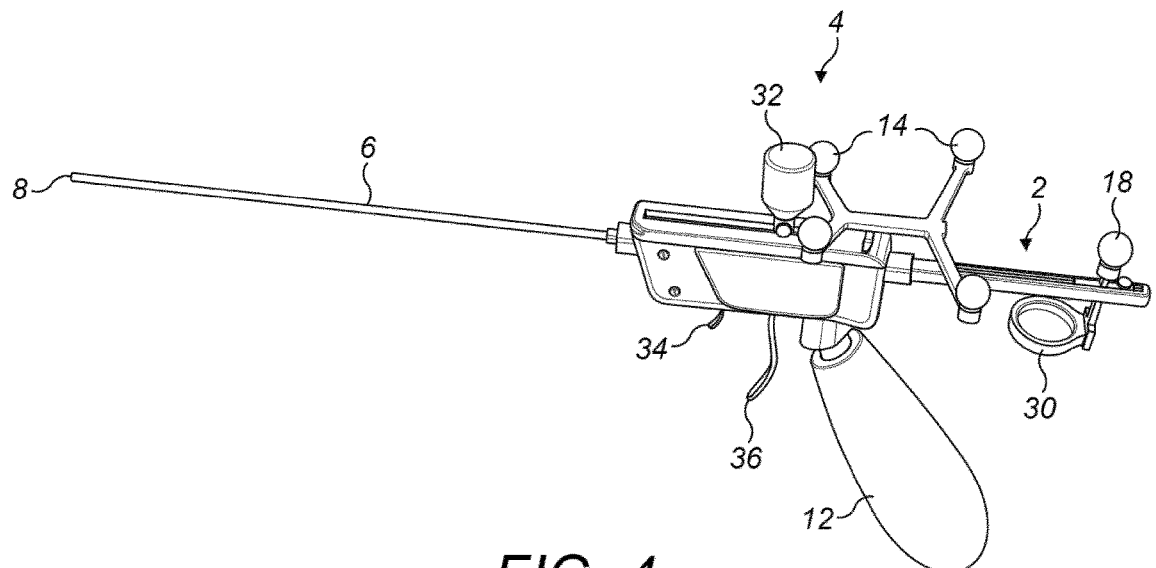
FIG. 4 is a perspective view of another example of an intervention device'.
Figure 5:
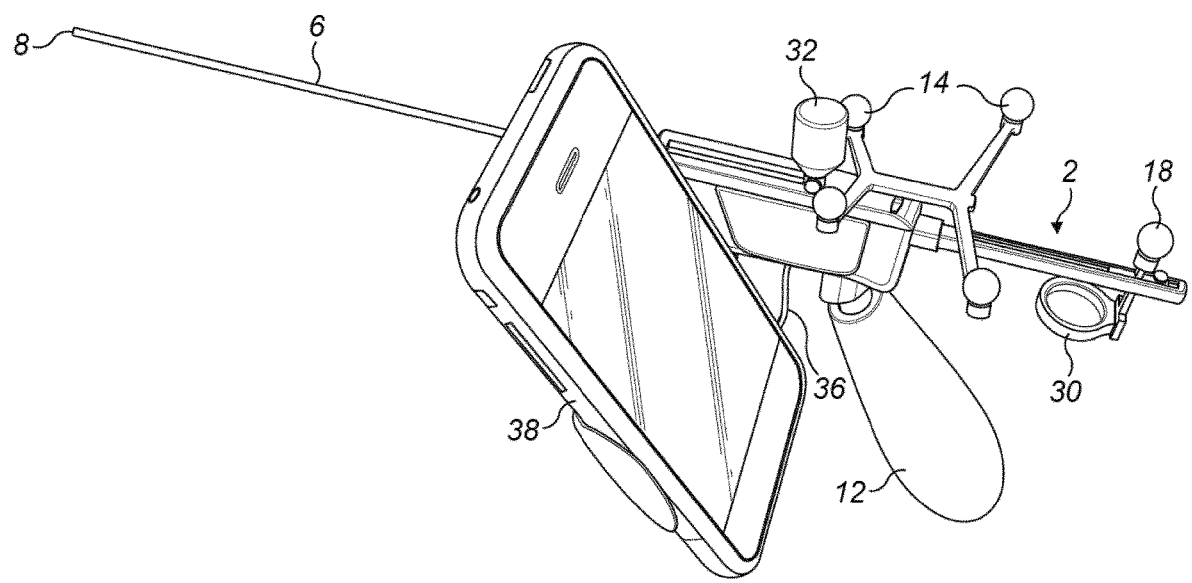
FIG. 5 shows the device of FIG. 4 with the addition of a handheld device mounted to the body of the intervention device.

Another exemplary intervention device is shown in FIGS. 4 and 5. This device has generally similar features to the device described in relation to FIG. 1 and comprises the same main parts, with a proximal piece 2, body section 4 and end piece 6. With the perspective views of FIGS. 4 and 5 the arrangement of the array 14 of reflector balls can be more clearly seen, in particular the spacing of the front and rear pairs of balls 14. This arrangement is also found in the device of FIG. 1.

The example device of FIGS. 4 and 5 includes various additional or alternative features compared to the device of FIG. 1. The differences are in the proximal piece 2 and body section 4, and also in the supply of fluid to the needle. If not described otherwise then the remaining features can be taken to be similar or identical to the features described above for FIG. 1. The proximal piece 2 includes a handle in the form of a ring 30 for enabling the user to push or pull the instrument with the thumb or a finger. In this way the needle can be moved in a one-handed operation whilst the handle 12 of the body section is held by the same hand. A reflector 18 is attached to the ring 30 to permit the navigation system to determine the position of the needle as it moves with movement of the ring 30. To supply fluid to the needle the device of this second example includes an ampule 32 attached to the needle within the body section 4. There are also further features for actuating the device in the form of two trigger levers 34, 36. The body section 4 incorporates a locking mechanism to lock needle in place and prevent further movement of the proximal piece, and this is actuated using a first, shorter, lever 34. A second, longer, lever 36 is provided for actuating a mechanism that aspirates and then injects a substance from the ampule 32.

It will be seen that FIG. 5 includes an additional feature of a handheld device 38, which is not in FIG. 4. The handheld device 38 is mounted to the body section 4 and can operate as discussed above in order to assist the user with navigation.

Figure 6:
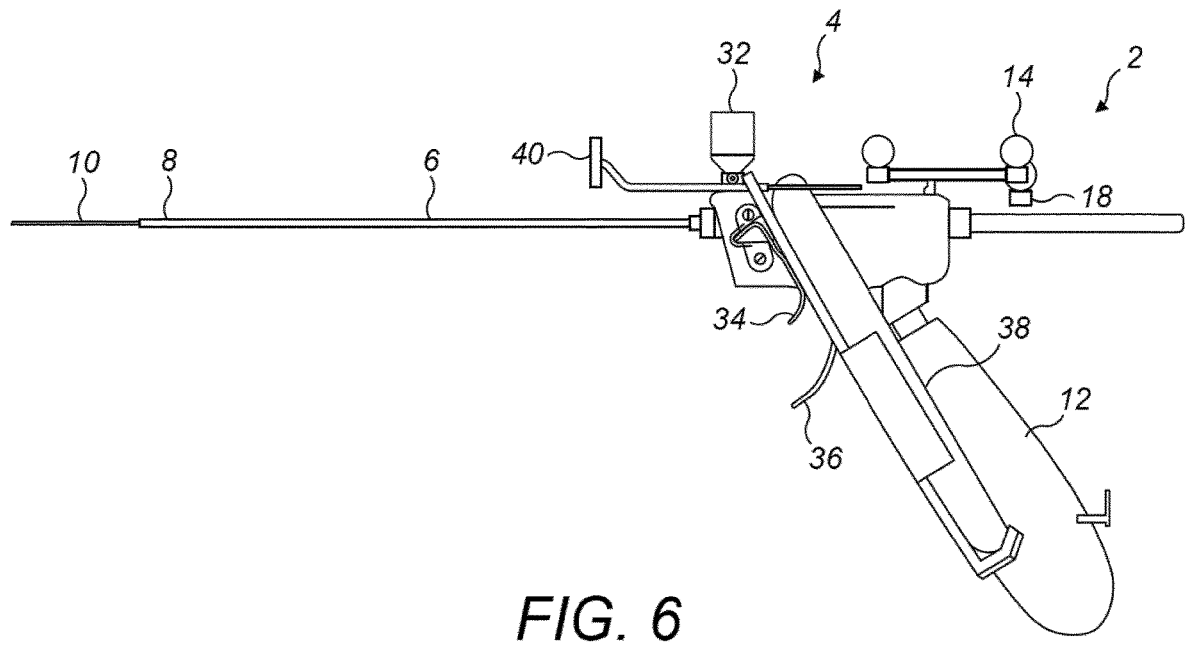
FIGS. 6 and 7 are side and end views of a device similar to the device of FIG. 5.
Figure 7:
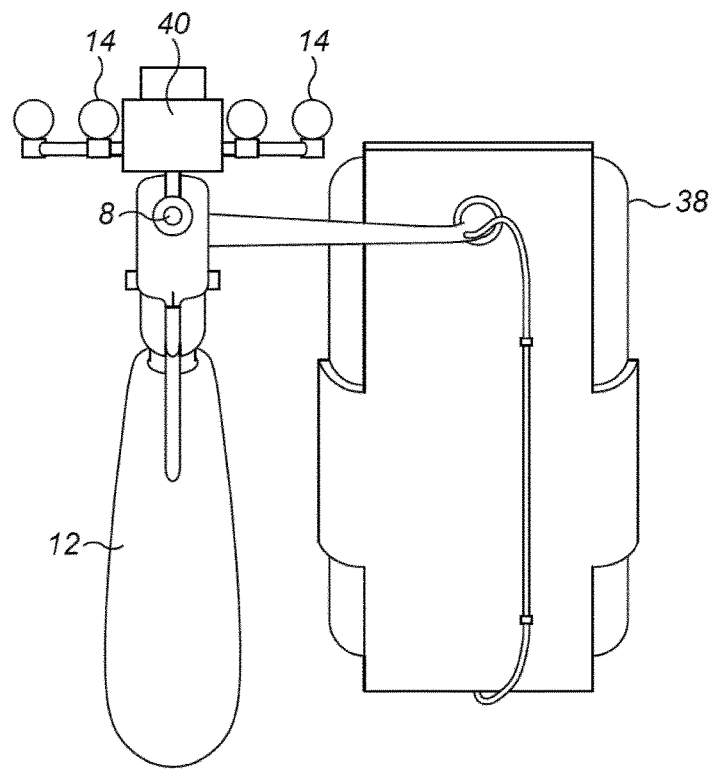

FIGS. 6 and 7 show a similar device to that shown in FIG. 5, but with an additional feature of a cheek-stopper 40. The other features are as in FIG. 5, although for this example the ring 30 is omitted. FIG. 6 is a side view and FIG. 7 is an end view looking along the line of the end piece 6 from the tip 8 toward the body section 4. It should also be noted that whilst FIGS. 4 and 5 show the needle 10 in a retracted position, withdrawn within the end piece 6 and hence not visible, FIG. 6 shows the needle 10 extended out of the tip 8 of the end piece 6. The reflector 18 clamped to the needle 10 at the proximal piece 2 is hence moved forward by the same distance that the needle 10 has moved.

Figure 8:
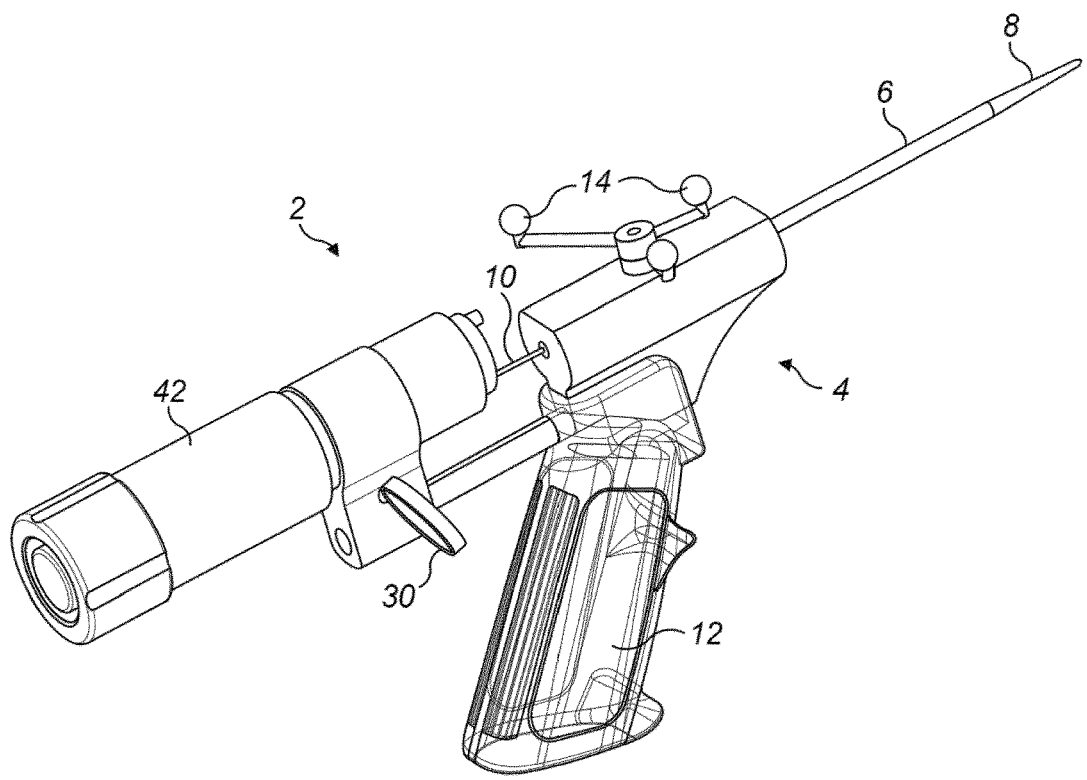
FIG. 8 is a perspective view of a further example of an intervention device.
Figure 9:
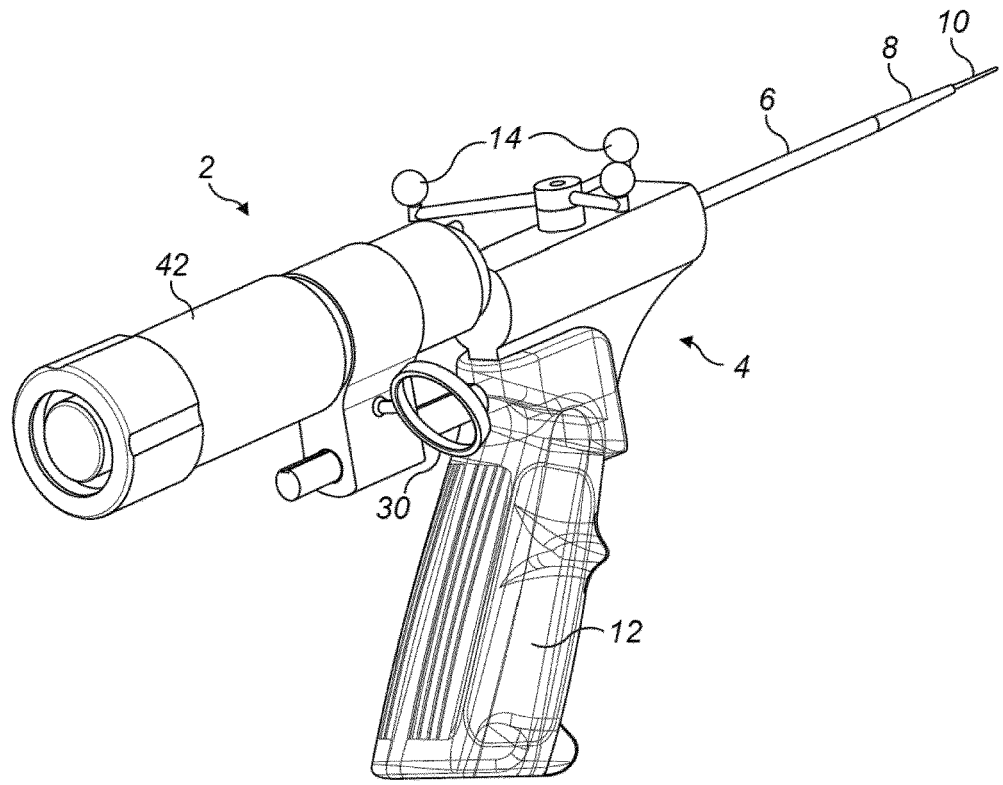
FIG. 9 shows the intervention device of FIG. 8 with the needle extended.

A further example of an intervention device is shown in FIGS. 8 and 9. The device is broadly similar to the other examples herein, but the design of the handle 12 is changed and a three reflector navigation array 14 is used in place of the four reflector navigation array 14 of the above devices. In addition, in place of the luer lock 28 or ampule 32, the device of FIGS. 8 and 9 includes a core biopsy instrument 42 to take core needle biopsy. An example of a suitable instrument for the core biopsy instrument 42 is the BARD® MONOPTY® Disposable Core Biopsy Instrument, as manufactured by Bard Peripheral Vascular Inc., of Tempe, Ariz., USA. See www.bardbiopsy.com. Another possible biopsy instrument is the BARD® MAGNUM® Resuable Core Biopsy Instrument, from the same manufacturer. The core biopsy device 42 is connected to a slide at the proximal piece 2 and can be moved by way of a ring 30 that is operable via a finger or thumb. FIG. 8 shows the needle 10 withdrawn inside the end piece 6 and FIG. 9 shows the core biopsy instrument 42 slid forward and the needle 10 therefore extending from the tip 8 of the end piece 6.

Figure 10B:
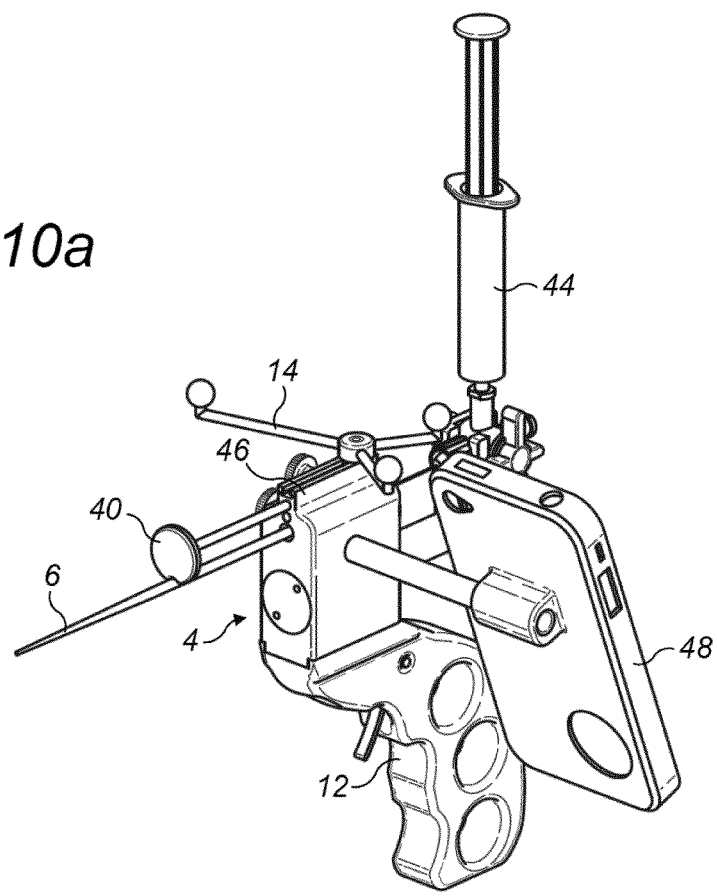

FIGS. 10a and 10b show another example device, which once again is broadly similar to the other examples described herein. In these Figures the reference numbers show similar features to those described above, including the proximal piece 2, body section 4, end piece 6 and tip 8. The navigation array 14 has three reflectors similar to the example of FIGS. 8 and 9. The device of FIGS. 10a and b has a syringe 44 connected to the needle 10 via the proximal piece 2. The syringe 44 can be coupled to the needle 10 using any suitable coupling mechanism, for example a three-way stop cock. The device further includes a cradle 48 for a handheld device 38. The handheld device 38 can be used as described above to assist in the intervention procedure. A cheek stopper 40 is also present. It will be appreciated that the device of FIGS. 10a and b could be used without the cradle 48 and cheek stopper 40, if required.

The device of FIGS. 10a and 10b further includes a track 46 on the body section 4, in which the navigation array 14 is mounted. The track 46 allows the navigation array 14 to slide along the body section, although in the arrangement of the Figures this feature is not in use and the navigation array would instead be fixed in place. When the sliding connection is used the instrument (the needle 10 in this example) would be connected to the navigation array 14 via a coupling between the proximal piece 2 and the array 14. This is to allow the array 14 to be rigidly connected to the instrument and to hence reflect the location of the instrument within the body.

Another example device is shown in FIGS. 11a and 11b. The main features are similar to the example of FIGS. 10a and 10b, but the syringe is not present and instead an endoscope 52 is mounted on the body section 4. Advantageously, the endoscope 52 can be linked to the display of a smart phone 38 mounted in smartphone cradle 48 so that the smart phone 38 shows the endoscope 52 image feed. This allows the view from the endoscope 52 to be easily seen by the user and also to be aligned with the orientation of the device/end piece 6. As noted above, fitting the device with an endoscope 52 enables convenient combined use of the endoscope 52 with other instruments, such as a needle 10, without risk of collision of the two instruments.

The further example of FIG. 12 is similar to that of FIGS. 10a and 10b, but the cradle 48 and cheek stopper 40 have been removed and the syringe 44 is replaced with a core biopsy instrument 42, similar to that discussed above. Once again the body section 4 has a track 46 that the navigation array 14 is mounted in for sliding movement. The movable proximal piece 2 is connected to the navigation array 14 by a coupling so that when the biopsy instrument 42 is moved then the navigation array 14 also moves. FIG. 11 also shows a handle 12 made of a transparent material, which is an optional feature. The internal mechanism of the device can be seen. In this example a trigger is provided to actuate the device and cause the biopsy instrument and the needle to advance.

It should be noted that the features of the needle tip described in relation to FIG. 2 and the various alternative embodiments of the tip 8 of the end piece 6 shown in FIG. 3 can also be utilised in the devices shown in FIGS. 4 to 12. Similarly, the additional features of FIGS. 4 to 12 relating to the handheld device 38/cradle 48, ring 30, ampule 32 and lever system, sliding track 46, syringe 44, cheek stopper 40, core biopsy instrument 42, endoscope 52 and so on can also be used with the device of FIG. 1 or as optional features for any of the other devices of FIGS. 2 to 12.

The devices described above makes it safe to use the lateral approach targeting the SPG, significantly lowering the risk of complications such as tissue destruction of adjacent structures by the very instrument at use or adverse events due to misjudged placement of the needle while injecting the pharmacological substance. At the same time the positioning of the injection will be highly accurate, making it feasible to use small volumes with minimal possibilities of diffusion into adjacent structures. Such a precision also ensures optimal delivery of the pharmacological substances and therefore optimal treatment effect.

In further alternative embodiments the end piece 6 and tip 8 can be designed for implantation of neuromodulators where, for example, the very end of the neuromodulator can be pointed and pushed out of the device to be installed at the target site as applicable. The distal end can alternatively, be formed to carry an implant, for example a steroid releasing implant to be installed in sinuses. The device may also be adapted for other procedures such as those listed below.

The end piece 6 can also be adjusted in design by providing it with anchor points for flexible or rigid endoscopes. An endoscope may alternatively be mounted on the body section of the device, as in the example of FIGS. 11a and 11b. Use of an endoscope would ease the localisation of the best entry point on the lateral wall of the nasal cavity using the transnasal route, making this procedure more user friendly and more accessible as procedure performed under local anaesthesia. An endoscope can also assist with other procedures using the device.

In the case of electromagnetic navigation, which can be used as an alternative or in addition to optical navigation, a coil can be embedded in the tip 8 and/or the end piece 6.

Example dimensions for the end piece are set out in the table below. The example end pieces are manufactured of beta titanium and available from Futaku Precision Machinery Industry Company of Kyoto, Japan. Alternative sizes could of course be used, provided that they have sufficient rigidity.

| Straight/angled tip | Length To the angled segment (cm) | Total (cm) | Outer diameter Proximal (mm) | Distal (mm) | Inner diameter (mm) |
|---|---|---|---|---|---|
| Straight | | 14 | 3.048/1.651 | 1.10 | 0.9 |
| 45 degrees | 14 | 16 | 3.048 | 1.270 | 1.1 |
| Straight | | 16 | 3.048 | 1.40 | 1.1 |
| 20 degrees | 14 | 16 | 3.048 | 1.651 | 1.3 |
| 40 degrees | 14 | 16 | 3.048 | 1.70 | 1.6 |
| Straight | | 16 | 3.048 | 1.270 | 0.9 |
| 20 degrees | 14 | 16 | 3.048 | 1.270 | 1.1 |
| 40 degrees | 14 | 16 | 3.048 | 1.45 | 1.3 |
| Straight | | 18 | 3.048 | 2.10 | 1.6 |

A possible advantageous use of the device is the injection of neuroinhibitory substances such as botulinum toxin in close proximity to the SPG or OG. Note that the injection device should not penetrate the SPG or OG. The injection is achieved in order to treat or prevent headache and may be achieved without damage to surrounding critical structures within the head. A neuroinhibitor is defined as any substance that affects transmission in a neural structure, resulting in any change of transmission, which may decrease or increase the neural activity. The neuroinhibitory substance is preferably a neurotoxin.

By delivery of the active substance in close proximity (proximally) to the sphenopalatine ganglion or otic ganglion means that the botulinum toxin or other neuroinhibitory substance in question is delivered so that it causes the desired technical effect, e.g. the prevention of treatment of headache etc. Ideally therefore the neuroinhibitory substance is injected to within 5 mm of the SPG or OG, preferably within 4 mm, such as within 3 mm, especially within 2 mm. Ideally injection of the active ingredient takes place 2 mm or less form the target SPG or OG. This can be measured using the device and associated computer technology which is described in detail below.

The injection of the neuroinhibitor occurs infrazygomatically or transnasally in order to ensure that a safe, close injection of the neuroinhibitor is achieved. The terms infrazygomatic or transnasally are terms of this art.

The term infrazygomatic therefore requires that the injection takes place inferior to the zygomatic arch on either side of the mandibula, typically anterior or through the mandibular notch.

The term transnasally defines an injection route which involves advancing the needle through the nasal cavity. Targeting the SPG this route will further violate the lateroposterior boundary of the nasal cavity, constituting the medial boundary of the SF.

Targeting the OG involves advancing through the maxillary ostium and the maxillary sinus, violating the back wall of the maxillary sinus, advancing on the lateral aspect of the lateral pterygoid plate. The OG is located in the infratemporal fossa, the SPG in the sphenopalatine fossa.

It is preferably the case that access to the SPG or OG from the outside of the body is achieved infrazygomatically or transnasally by insertion of the injection device such that the device defines a straight line between SPG or OG (or more specifically the point proximal to the SPG and OG where active substance release will occur) and the point at which the external skin or mucosa is penetrated. This is illustrated in FIGS. 13, 15 and 16. FIG. 14 shows an alternative preferred approach where the end piece of the device has a curved tip enabling the needle to be directed toward the SPG or OG at an angle from the main axis of the lumen. The device punctures the wall of the nasal cavity at puncture site 50 and the angled tip directs the needle toward the target site.

The infrazygomatic approach therefore allows the injection device to pass through the skin and then soft tissue to the SPG or OG. That can be achieved in a straight line and hence with a straight injection device. That means that the injection can be targeted very accurately in close proximity to the SPG or OG. This method of administration allows application under local anaesthetic.

Where the injection takes place transnasally the route involves passing through the nasal mucosa and the sphenopalatine foramen or the perpendicular plate of the palatine bone to reach the SPG. Injection is not therefore lateral (via the cheek) but preferably involves a straight line from the injection point to the SPG. Transnasal route to reach the OG involves advancing through the maxillary ostium and the maxillary sinus, violating the back wall of the maxillary sinus, advancing on the lateral aspect of the lateral pterygoid plate. This involves a straight line from the injection site to the OG. These methods may require general anaesthesia.

The injection described above can be used in the treatment or prevention of headaches, in particular any kind of primary headache or secondary headache. The treatment or prevention may relate therefore to cluster headaches, migraine, tension-type headache, short lasting unilateral neuralgiform headache with conjunctival injection and tearing/cranial autonomic features (SUNCT/SUNA), hemicrania continua or paroxysmal hem icrania.

Paroxysmal hemicrania is a primary headache disorder involving frequent attacks of unilateral, peri-orbital and temporal pain typically lasting less than 30 minutes. The pain can be associated with conjunctival injection, lacrimation, nasal congestion, rhinorrhea, ptosis and eyelid edema.

SUNCT/SUNA is a primary headache disorder characterized by multiple attacks of unilateral, peri-orbital and temporal pain typically lasting less than 2 minutes. The pain is associated with conjunctival injection, lacrimation, nasal congestion, rhinorrhea, and eyelid edema. This headache may be associated with trigeminal neuralgia.

Hemicrania continua is a primary headache disorder characterized by a strictly unilateral headache responsive to Indomethacin. The pain is associated with conjunctival injection, lacrimation, nasal congestion, rhinorrhea, ptosis, and eyelid edema.

It will be appreciated that the term treatment here refers to reduction in pain experienced by a patient and/or a reduction in the frequency in which headache occurs. The term prevention means preventing headaches occurring, e.g. as frequently as before.

The neuroinhibitory substance is one which is capable of preventing or treating headache when administered in close proximity to the SPG or OG. Suitable inhibitors include Botulinum toxin, Tetanus neurotoxin, (which is produced by *Clostridium tetani*), Staphylococcal alpha-toxin, and acyl-polyamine toxins (e.g. AR636 and AG489).

In general the therapeutic modality used to treat and/or prevent headache is a presynaptic neurotoxin. "Presynaptic neurotoxin" as used herein refers to those neurotoxins and their derivatives which are known to produce localized, reversible flaccid paralysis of musculature in mammals which does not result in degeneration of muscle or nervous tissue.

It is preferred however if the inhibitor is botulinum toxin. This is a protein and neurotoxin produced by the bacterium *Clostridium botulinum* and is commercially available. It is preferred if the botulinum toxin is of types A, B, C, D, E, F or G, such as Botulinum toxin type A. Botulinum toxin may for example be administered in the manner and form described in U.S. Pat. No. 7,981,433

The frequency of the injections needed may be every 3 to 8 months but will be patient dependent.

Whilst the method described above is in relation to the administration of neuroinhibitory substances such as botulinium toxin, the method of injection and device discussed here can be used for the injection of other active substances such as local anaesthetics (e.g. lidocaine or marcain) and corticosteroids (e.g. triamcinolone). The method and device may be used to inject a local anaesthetic or corticosteroid for use in a method for treating or preventing headache, rhinitis, rhinosinusitis, Frey syndrome or hypersecretion of tears/lacrimation comprising injecting said substance in close proximity to the sphenopalatine ganglion or otic ganglion wherein an injection device comprising said substance is brought into close proximity to the sphenopalatine ganglion or otic ganglion by inserting said injection device into the patient transnasally or infrazygomatically and the substance injected in close proximity to the SPG or OG.

Various example procedures using the device described above are set out below and FIGS. 13*a* through 16 illustrate the locations of the SPG and OG along with possible approaches for interventions on the SPG or OG as discussed above.

EXAMPLE 1

A female patient with refractory hemicrania continua was treated via injection of Botox around the SPG. Due to an occipital neurostimulator MRI was contraindicated and identification of SPG on MRI was not possible. Preoperatively the calculated position of the SPG was marked on a CT scan with 1 mm slides. On the navigation planning system a preplanned puncture site and trajectory was made. On the symptomatic side a navigable needle guide was advanced through the sphenopalatine foramen and towards the SPG. The needle was passed through the guide and the tip of the needle was confirmed to be 1 mm from the SPG by the navigation system while 75 IU botulinum toxin type A was injected.

Over a period of two months prior to the treatment the patient had an average headache intensity of 8.1 (scale 1-10) and normally experienced from one to four headache attacks daily. From 4 to 10 weeks after the treatment the patient had not a single attack during the whole period and the average headache intensity was 6.3. The patient also did not experience any complication during 4 months follow-up.

EXAMPLE 2

The patient was a male that presented with a prevertebral mass close to the atlas (C1) seen on MRI. He had formerly been treated for pulmonary cancer histologically classified as adenocarcinoma. After a clinical assessment it was concluded that the tumor was not available for conventional procedures for a histological diagnosis. Using a navigable guide with an optical navigation system and a transoral approach it was possible to do a fine needle biopsy of the tumor deep in the neck to confirm the suspicion of a pulmonary metastasis.

EXAMPLE 3

A female patient with refractory chronic cluster headache was treated via injection of lidocaine around the OG. Preoperatively the calculated position of the SPG was marked on a CT scan with 1 mm slides. On the navigation planning system a pre-planned puncture site and trajectory was made. On the symptomatic side a navigable needle guide was advanced through the maxillary ostium and the back wall of the maxillary sinus, and then at the lateral aspects of the lateral pterygoid plate to the OG. 5 ml of lidocaine 20 mg/ml was injected. The patient had a short relief of the headache as expected using short-acting local anaesthetic.

EXAMPLE APPLICATIONS

The advantages for interventions targeting the SPG will also arise when using the device for IGS in the rest of the body for indications such as injections, biopsies, punctures, aspiration, ablation therapy, and for positioning of electrodes, catheters, radioactive seeds and implants. The same device can be used or it may be advantageous to use a similar device with an alternative tip design or a different length of end piece, depending on the characteristics of the target site, the approach available and the procedure that is to be carried out. The needle guide device may thus be utilised for procedures to address numerous medical conditions. Procedures that the device can be used for include:

- Injections
  - Any pharmacological substance
  - Neuroexcitatory agent
  - Neuroinhibitory agents
  - Botulinum toxin, any type
  - Staphylococcal alpha-toxin
  - Tetanus neurotoxin
  - Acylpolyamine toxins
- Core needle biopsy and fine needle biopsy
  - Head/neck area
    - Intracranially
    - Extracranially
      - Retropharyngeal space
      - Parapharyngeal space
      - Skull base
      - Deep regions of the face/neck
      - Any region of the face/neck
    - In the vicinity of the columna In the vicinity of bone in any region of the body
  Any region of the body
Puncture and aspiration
  Evacuation of cystic structures and fluidic compartment for diagnosis and therapy
  Any part of the body
Ablation therapy
  Any nerve or neural structure, intracranially and extracranially
  Ablation of normal tissue to reduce volume and/or increase stiffness in any region of the body
  Ablation of tumour tissue in any region of the body
Positioning of electrodes, catheters, implants, electrophysiological measurements, radioactive seeds
  Any structure or organ of the body including nerve, neural structure, blood vessel.
Endoscopy and/or pointer procedures
  Flexible or rigid endoscope may be attached to the device
  Any procedure in an open cavity that requires endoscope or pointer
  Paranasal sinusis
  Nasal cavity
  Farynx
  Larynx
The device can be used in the treatment of conditions including:
  Headache
    Migraine
    Cluster headache
    Tension-type headache
    Trigeminal Autonomic Headache
    SUNCT
    Hemicrania Continua
    Paroxysmal hemicrania
    Any kind of primary headache
    Any kind of secondary headache
  Rhinitis
    Allergic rhinitis
    Vasomotor rhinitis
    Rhinitis medicamentosa
    Polypous rhinitis
    Any kind of non-structural rhinitis
  Rhinosinusitis
    Without polyps
    With polyps
    Any kind of rhinosinusitis
  Hypersecretion of tears/excessive lacrimation
    Any disease with hypersecretion of tears
  Frey syndrome/auriculotemporal syndrome/gustatory sweating
  Tinnitus
    Objective tinnitus
    Subjective tinnitus Whilst the indications and examples above primarily relate to conditions of the human body the device can of course also be utilised for interventions on the animal body.

The invention claimed is:

1. A device adapted for interventions within a patient's body, the device comprising:
   an end piece adapted to be inserted into the patient's body at a distal end of the end piece, the end piece including a rigid lumen for holding an instrument and guiding slidable movement of the instrument to the distal end of the end piece;
   a body section supporting the lumen and being rigidly connected thereto;
   a navigation array rigidly connected to the instrument and held in a track on the body section that permits slidable movement of the navigation array relative to the body section, the navigation array comprising a plurality of optical markers at known locations relative to the end piece or an electromagnetic location sensor at a known location relative to the end piece, and wherein the navigation array is configured to allow for guidance of the device in three dimensions toward a target site within the patient's body using a surgical navigation system;
   a proximal holder piece configured to hold a proximal end of the instrument, the proximal holder piece being positioned at a proximal end of the end piece and of the body section;
   one or more clamps configured to attach to the instrument, wherein the one or more clamps are configured to fix the instrument in place relative to the end piece and the distal end of the end piece thereof; and
   moveable parts configured to connect to and move with the instrument as the instrument moves slidably relative to the end piece;
   wherein an entirety of the body section, with the navigation array connected thereto, is placed/positioned between the end piece and the proximal holder piece, wherein the instrument extends from a proximal end of the proximal holder piece, through the body section and into the lumen of the end piece, and wherein the slidable movement of the instrument relative to the end piece moves the instrument along the lumen and through the distal end of the end piece into the patient's body.

2. The device of claim 1, wherein the distal end of the end piece comprises a tip adapted to pierce the patient's body, the tip comprising a tapered profile narrowing toward a point.

3. The device of claim 1, wherein the end piece comprises a marking adapted to show a depth of insertion of the end piece into the patient's body.

4. The device of claim 1, wherein the lumen is configured to be rigid enough to permit placement of a tip of the end piece with millimeter accuracy without deformation as the lumen penetrates body tissues and while being subject to any bending moments that arise as the lumen is manoeuvred along a selected approach toward the target site.

5. The device of claim 4, wherein the device is adapted to be used for cranial use and the rigidity of the lumen is sufficient to enable the tip to be placed with millimeter accuracy at the patient's sphenopalatine ganglion or otic ganglion when targeted via a lateral approach.

6. The device of claim 5, wherein the device is adapted to be used for cranial use and the of the lumens is sufficient to limit deflection of the instrument as the instrument advances toward the patient's sphenopalatine ganglion along the lateral approach to a deflection of from 0 mm to 2 mm per 10 cm of length of the lumen.

7. The device of claim 1, wherein the rigid connection between the navigation array and the instrument is via a coupling between the proximal holder piece and the navigation array.

8. The device of claim 1, wherein the instrument further comprises an injection needle configured to inject substances into the patient's body, and the end piece is for receiving and guiding the needle.

9. The device of claim 1, wherein the lumen is sized to receive a needle having a diameter of 25 G or smaller (diameter of 0.02025 inches or smaller).

10. The device of claim 1, the instrument further comprising a needle, the needle including a needle tip comprising a slightly rounded end and openings on each side of the tip rather than at the tip end.

11. The device of claim 10, further comprising an ampule or a syringe, the ampule or the syringe being attached to the needle at the body section or at the proximal holder piece.

12. The device of claim 11, further comprising a first, locking, mechanism to lock the proximal holder piece and a second, injection, mechanism to aspirate and then inject a substance from the vessel.

13. The device of claim 1, wherein the instrument is a pointer, a neurostimulator, a core biopsy needle, a fine biopsy needle, an electric or radiofrequency ablation therapy electrode or a cannula for chemical ablative therapy.

14. A method comprising: inserting the device of claim 1 into the body and using the surgical navigation system to guide the instrument, the end piece, or both in three dimensions toward the target site within the patient's body, the navigation system being associated with the navigation array of the device.

15. The method of claim 14, wherein the instrument is a needle, the method further comprising injecting a pharmacological substance into the patient's body at the target site.

16. The method of claim 14, wherein the navigated insertion of the end piece of the device is toward a sphenopalatine ganglion or otic ganglion along a lateral approach.

17. An apparatus comprising a computer processor and a computer-readable medium storing computer-executable instructions that when executed cause the apparatus to perform a method comprising: configuring an image guided surgery navigation system to guide the end piece of the device of claim 1 in three dimensions toward the target site within the patient's body.

18. The apparatus of claim 17, wherein the instructions, when executed, cause the apparatus to configure the image guided surgery navigation system to guide the end piece in three dimensions toward the patient's sphenopalatine ganglion or otic ganglion along a lateral approach.

* * * * *